(12) United States Patent
Brown et al.

(10) Patent No.: US 7,482,487 B2
(45) Date of Patent: Jan. 27, 2009

(54) PHENYLAMINOETHANOL DERIVATIVES AS β2 RECEPTOR AGONISTS

(75) Inventors: Alan Daniel Brown, Sandwich (GB); Justin Stephen Bryans, Sandwich (GB); Paul Alan Glossop, Sandwich (GB); Charlotte Alice Louise Lane, Sandwich (GB); Simmon John Mantell, Sandwich (GB)

(73) Assignee: Pfizer Inc, New York, NY (US)

( * ) Notice: Subject to any disclaimer, the term of this patent is extended or adjusted under 35 U.S.C. 154(b) by 52 days.

(21) Appl. No.: 10/598,843

(22) PCT Filed: Mar. 10, 2005

(86) PCT No.: PCT/IB2005/000611

§ 371 (c)(1), (2), (4) Date: Jun. 15, 2007

(87) PCT Pub. No.: WO2005/090288

PCT Pub. Date: Sep. 29, 2005

(65) Prior Publication Data

US 2007/0264262 A1    Nov. 15, 2007

Related U.S. Application Data

(60) Provisional application No. 60/591,854, filed on Jul. 27, 2004.

(30) Foreign Application Priority Data

Mar. 17, 2004  (EP) ................. 04290724
Mar. 10, 2005  (EP) ................. 05708707

(51) Int. Cl.
*C07C 233/05* (2006.01)
*A61K 31/65* (2006.01)

(52) U.S. Cl. ............ 564/165; 514/595; 514/596; 514/616; 514/620; 564/48; 564/56; 564/86; 564/155; 564/158

(58) Field of Classification Search .......... 564/165, 564/48, 56, 86, 155, 158; 514/620, 595, 514/596, 603, 616
See application file for complete search history.

(56) References Cited

U.S. PATENT DOCUMENTS 3,644,353 A      2/1972  Lunts et al. ............. 260/247.5
7,268,147 B2 *   9/2007  Bunnage et al. .......... 514/307

OTHER PUBLICATIONS

Collin et al., J. Med. Chem., vol. 13, No. 4, pp. 674-680, 1970.

* cited by examiner

*Primary Examiner*—Shailendra Kumar
(74) *Attorney, Agent, or Firm*—Gregg C. Benson; Robert T. Ronau

(57) ABSTRACT

The invention relates to compounds of formula (1) and to processes for the preparation of, intermediates used in the preparation of, compositions containing and the uses of, such derivatives. The compounds according to the present invention are useful in numerous diseases, disorders and conditions, in particular inflammatory, allergic and respiratory diseases, disorders and conditions.

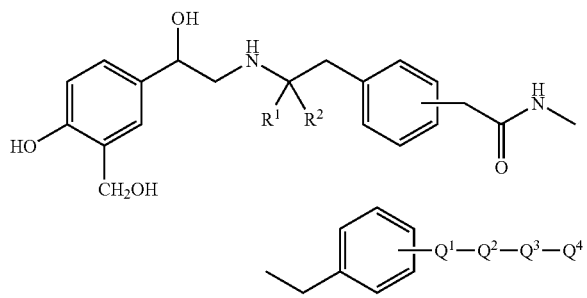

(1)

12 Claims, No Drawings

PHENYLAMINOETHANOL DERIVATIVES AS β2 RECEPTOR AGONISTS

This application is a 371 of PCT/IB05/00611 Mar. 10, 2005 which claims benefit of 60/591,854 Jul. 27, 2004.

This invention relates to β2 agonists of general formula:

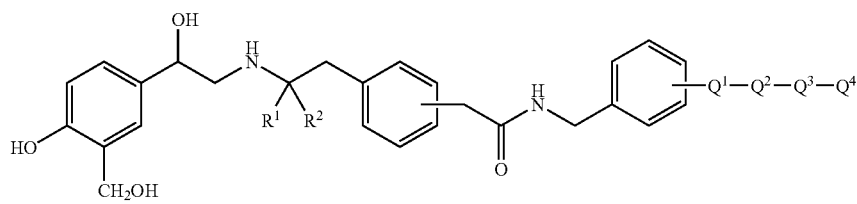

(1)

in which $R^1$, $R^2$, $Q^1$, $Q^2$, $Q^3$ and $Q^4$ have the meanings indicated below, and to processes for the preparation of, intermediates used in the preparation of, compositions containing and the uses of, such derivatives.

Adrenoceptors are members of the large G-protein coupled receptor super-family. The adrenoceptor subfamily is itself divided into the α and β subfamilies with the β sub-family being composed of at least 3 receptor sub-types: β1, β2 and β3. These receptors exhibit differential expression patterns in tissues of various systems and organs of mammals. β2 adrenergic (β2) receptors are mainly expressed in smooth muscle cells (e.g. vascular, bronchial, uterine or intestinal smooth muscles), whereas β3 adrenergic receptors are mainly expressed in fat tissues (therefore β3 agonists could potentially be useful in the treatment of obesity and diabetes) and β1 adrenergic receptors are mainly expressed in cardiac tissues (therefore β1 agonists are mainly used as cardiac stimulants).

The pathophysiology and treatments of airway diseases have been extensively reviewed in the literature (for reference see Barnes, P. J. Chest, 1997, 111:2, pp 17S-26S and Bryan, S. A. et al, Expert Opinion on investigational drugs, 2000, 9:1, pp 25-42) and therefore only a brief summary will be included here to provide some background information.

Glucocorticosteroids, anti-leukotrienes, theophylline, cromones, anti-cholinergics and β2 agonists constitute drug classes that are currently used to treat allergic and non-allergic airways diseases such as asthma and chronic obstructive airways disease (COPD). Treatment guidelines for these diseases include both short and long acting inhaled β2 agonists. Short acting, rapid onset β2 agonists are used for "rescue" bronchodilation, whereas, long-acting forms provide sustained relief and are used as maintenance therapy.

Bronchodilation is mediated via agonism of the β2 adrenoceptor expressed on airway smooth muscle cells, which results in relaxation and hence bronchodilation. Thus, as functional antagonists, β2 agonists can prevent and reverse the effects of all bronchoconstrictor substances, including leukotriene D4 (LTD4), acetylcholine, bradykinin, prostaglandins, histamine and endothelins. Because β2 receptors are so widely distributed in the airway, β2 agonists may also affect other types of cells that play a role in asthma. For example, it has been reported that β2 agonists may stabilize mast cells. The inhibition of the release of bronchoconstrictor substances may be how β2 agonists block the bronchoconstriction induced by allergens, exercise and cold air. Furthermore, β2 agonists inhibit cholinergic neurotransmission in the human airway, which can result in reduced cholinergic-reflex bronchoconstriction.

In addition to the airways, it has also been established that β2 adrenoceptors are also expressed in other organs and tissues and thus β2 agonists, such as those described in the present invention, may have application in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

However, numerous β2 agonists are limited in their use due to their low selectivity or adverse side-effects driven by high systemic exposure and mainly mediated through action at β2 adrenoreceptors expressed outside the airways (muscle tremor, tachycardia, palpitations, restlessness). Therefore there is a need for improved agents in this class.

Accordingly, there is still a need for novel β2 agonists that would have an appropriate pharmacological profile, for example in terms of potency, selectivity, duration of action and/or pharmacodynamic properties. In this context, the present invention relates to novel β2 agonists.

EP 0654534 B1 and EP0939134 B1 disclose a process for the preparation of compounds of formula (XI):

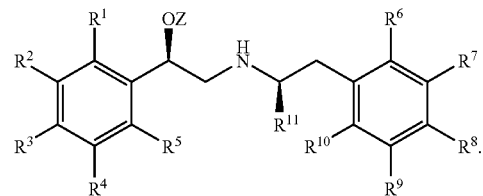

These compounds are disclosed as anti-obesity and anti-diabetic agents having specific β3 activity.

U.S. Pat. No. 5,561,142 discloses selective β3 agonists of formula

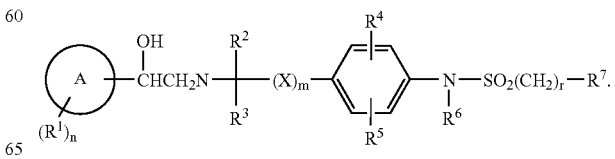

EP0236624 discloses compounds of formula

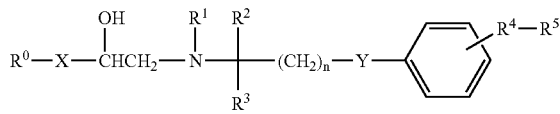

having anti-obesity and/or anti-hyperglycaemic activity coupled with good selectivity from cardiac side-effects.

The invention relates to compounds of general formula (1):

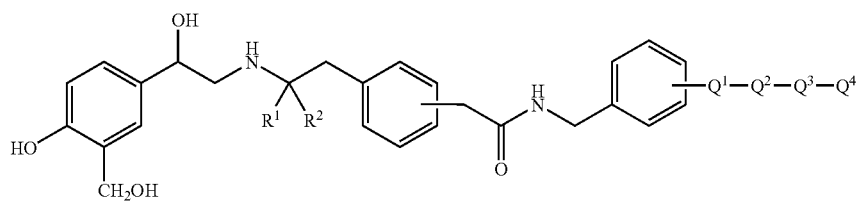

(1)

wherein the $CH_2$—$C(=O)NH$-benzyl-$Q^1$-$Q^2$-$Q^3$-$Q^4$ group is in the meta or para position, and $R^1$ and $R^2$ are independently selected from H and $C_1$-$C_4$ alkyl;

$Q^1$ is —$(CH_2)_n$— wherein n is an integer selected from 0 and 1;

$Q^2$ is a group selected from —NH—, —C(=O)NH—, —NHC(=O)—, —NH—C(=O)—NH—, and —$SO_2NH$—;

$Q^3$ is a single bond or a $C_1$-$C_4$ alkylene optionally substituted with OH;

$Q^4$ is selected from:

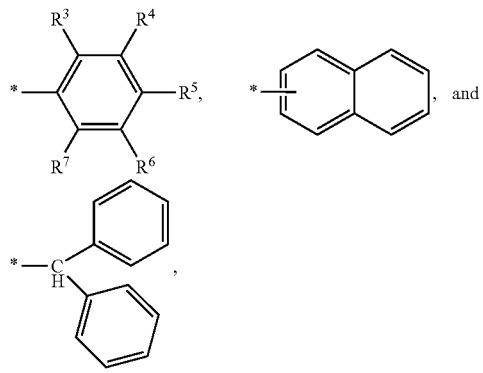

wherein * represents the attachment point to $Q^3$ and $R^3$, $R^4$, $R^5$, $R^6$ and $R^7$ are independently selected from H, $C_1$-$C_4$ alkyl, phenyl, phenoxy, $OR^8$, $SR^8$, halo, CN, $CF_3$, $OCF_3$, $COOR^9$, $SO_2NR^8R^9$, $CONR^8R^9$, $NR^8R^9$, $NHCOR^9$ and $CH_2$—$NHC(=O)NH$—$R^9$;

wherein $R^8$ and $R^9$ are independently selected from H or $C_1$-$C_4$ alkyl;

or, if appropriate, their pharmaceutically acceptable salts and/or isomers, tautomers, solvates or isotopic variations thereof.

It has now been found that the compounds of formula (1) are agonists of the β2 receptors, that are particularly useful for the treatment of β2-mediated diseases and/or conditions, and show good potency, in particular when administered via the inhalation route.

In the present invention, the term "potent" means that the compounds of formula (1) show an agonist potency for the β2 receptor, which is less than 10 nM as measured by the cell-based assay described herein.

Preferably, the compounds of the invention are potent and selective agonists of the β2 receptor receptors. More preferably, the compounds of the invention show an agonist potency for the β2 receptor, which is at least about 100-fold higher as for the β3 receptor and at least about 500-fold higher as for the β1 receptor.

In the here above general formula (1), $C_1$-$C_4$ alkyl and $C_1$-$C_4$ alkylene denote a straight-chain or branched group containing 1, 2, 3 or 4 carbon atoms. This also applies if they carry substituents or occur as substituents of other radicals, for example in O—($C_1$-$C_4$)alkyl radicals, S—($C_1$-$C_4$)alkyl radicals etc . . . . Examples of suitable ($C_1$-$C_4$)alkyl radicals are methyl, ethyl, n-propyl, iso-propyl, n-butyl, iso-butyl, sec-butyl, tert-butyl . . . . Examples of suitable O—($C_1$-$C_4$) alkyl radicals are methoxy, ethoxy, n-propyloxy, iso-propyloxy, n-butyloxy, iso-butyloxy, sec-butyloxy and tert-butyloxy . . .

Finally, halo denotes a halogen atom selected from the group consisting of fluoro, chloro, bromo and iodo in particular fluoro or chloro.

The compounds of the formula (1)

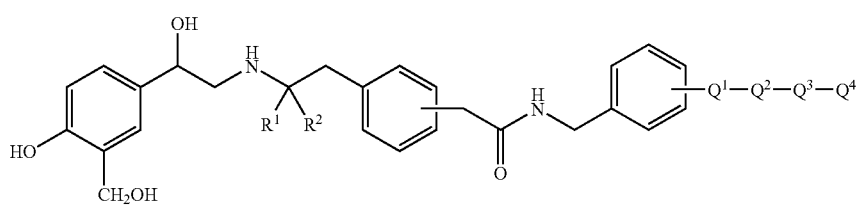

(1)

wherein the CH₂—C(=O)NH-benzyl-Q¹-Q²-Q³-Q⁴ group is in the meta or para position, can be prepared using conventional procedures such as by the following illustrative methods in which R¹, R², Q¹, Q², Q³ and Q⁴ are as previously defined for the compounds of the formula (1) unless otherwise stated.

The compounds of formula (1) may be prepared by deprotection of the compounds of formula (2):

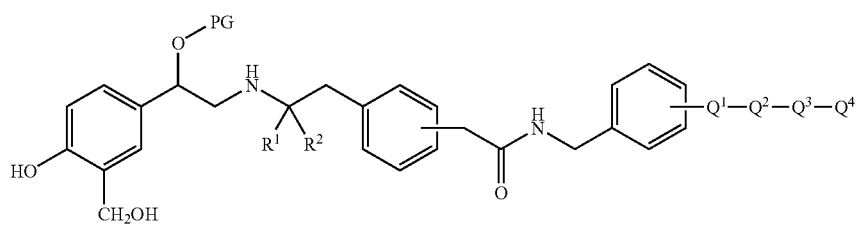

(2)

wherein the CH₂—C(=O)NH-benzyl-Q¹-Q²-Q³-Q⁴ group is in the meta or para position, where PG represents a suitable alcohol protecting group, typically an alkyl silyl group such as tert-butyidimethylsilyl (TBDMS) or trimethylsilyl (TMS), and preferably TBDMS.

The deprotection may be carried out according to the methods described in standard text-books such as "Protective Groups in Organic Synthesis" by T. W. Greene, A. Wiley-Interscience Publication, 1981. In a typical procedure, where PG represents TBDMS, the compound of formula (2) is treated with 10-20 eq ammonium formate in aqueous methanol, at about 40° C. for between 18 and 42 hours, or with aqueous acetic acid in tetrahydrofuran at between room temperature and about 65° C. for between 18 and 100 hours.

The amide derivatives of formula (2) may be prepared by coupling an acid of formula (3):

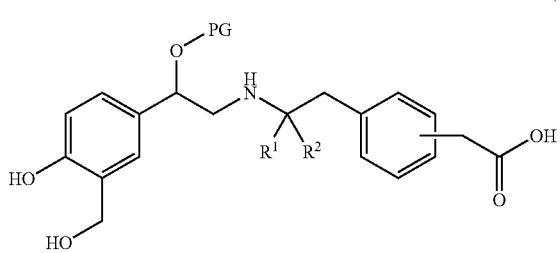

(3)

wherein the CH₂—C(=O)OH group is in the meta or para position with an amine of formula (4):

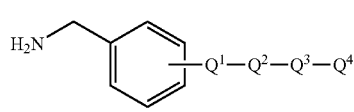

(4)

The coupling is generally carried out in an excess of said amine as an acid receptor, with a conventional coupling agent (e.g. 1-(3-dimethylaminopropyl)-3-ethylcarbodiimide hydrochloride or N,N'-dicyclohexylcarbodiimide), optionally in the presence of a catalyst (e.g. 1-hydroxybenzotriazole hydrate or 1-hydroxy-7-azabenzotriazole), and optionally in the presence of a tertiary amine base (e.g. N-methylmorpholine, triethylamine or N-diisopropylethylamine). The reaction may be undertaken in a suitable solvent such as pyridine, N,N-dimethylformamide, tetrahydrofuran, dimethylsulfoxide, dichloromethane or ethyl acetate, and at a temperature comprised between 10° C. and 40° C. (room temperature) for a period of 1-24 hours.

In a typical procedure, the acid of formula (3) is treated with an excess of amine of formula (4) (1.1-1.2 eq), 1-(3-dimethylaminopropyl)-3-ethylcarbodiimide hydrochloride (1.1-1.3 eq), 1-hydroxybenzotriazole hydrate (1.1-1.3eq) and triethylamine (2-3 eq) in N,N-dimethylformamide at room temperature for a period of 18 hours.

Said amine of formula (4) is either commercially available or may be prepared by conventional methods well known to the one skilled in the art (e.g. reduction, oxidation, alkylation, protection, deprotection etc . . . ) from commercially available material.

The acid of formula (3) may be prepared from the corresponding ester of formula (5):

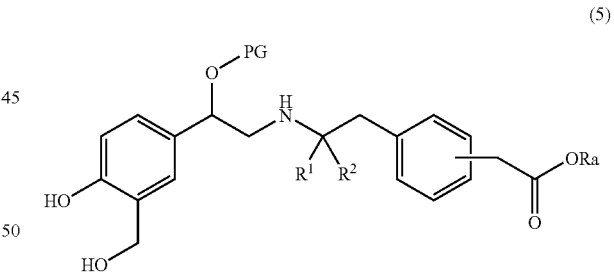

(5)

wherein the CH₂—C(=O)ORa group is in the meta or para position, wherein Ra is a suitable acid protecting group, preferably a (C₁-C₄)alkyl group, which includes, but is not limited to, methyl and ethyl, according to any method well-known to the one skilled in the art to prepare an acid from an ester, without modifying the rest of the molecule. For example, the ester may be hydrolysed by treatment with aqueous acid or base (e.g. hydrogen chloride, potassium hydroxide, sodium hydroxide or lithium hydroxide), optionally in the presence of a solvent or mixture of solvents (e.g. water, 1,4-dioxan, tetrahydrofuran/water), at a temperature comprised between 20° C. and 100° C., for a period of 1 to 40 hours.

In a typical procedure the ester of formula (5) is treated with an excess of lithium hydroxide (2 eq) in aqueous tetrahydrofuran atroom temperature for about 16 hours.

The ester of formula (5) may be prepared by deprotection of the compound of formula (6):

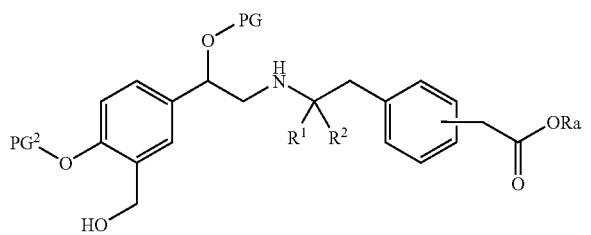

(6)

wherein the $CH_2-C(=O)ORa$ group is in the meta or para position, where $PG^2$ is a suitable phenol protecting group, typically an alkyl group, typically a methyl or benzyl group, and preferably a benzyl group.

The deprotection may be carried out according to the methods described in standard text-books such as "Protective Groups in Organic Synthesis" by T. W. Greene, A. Wiley-Interscience Publication, 1981.

In a typical procedure, wherein $PG^2$ is benzyl, the compound of formula (6) is hydrogenated in the presence of 10% palladium on charcoal in ethanol as solvent at 60 psi of $H_2$, for about 16 hours at room temperature.

The ester of formula (6) may be prepared by reaction of an amine of formula (7):

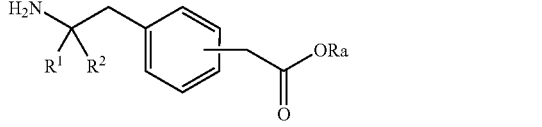

(7)

wherein the $CH_2-C(=O)ORa$ group is in the meta or para position and wherein Ra is as previously defined, with a bromide of formula (8):

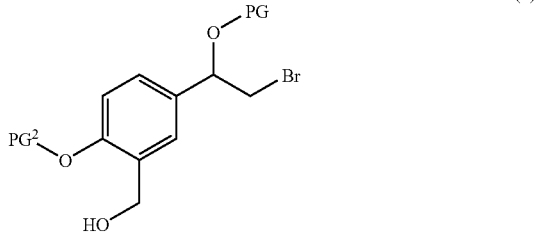

(8)

In a typical procedure, the amine of formula (7) is reacted with a bromide of formula (8) optionally in the presence of a solvent or mixture of solvents (e.g. dimethyl sulphoxide, toluene, N,N-dimethylformamide, acetonitrile), optionally in the presence of a suitable base (e.g. triethylamine, N-diisopropylethylamine, or potassium carbonate) at a temperature comprised between 80° C. and 120° C., for 12 to 48 hours.

Preferably, the amine of formula (7) (2 eq) and the bromide of formula (8) are reacted at 90° C. in the absence of solvent for about 16 hours.

The bromide of formula (8) may be prepared by reduction of the ester of formula (9):

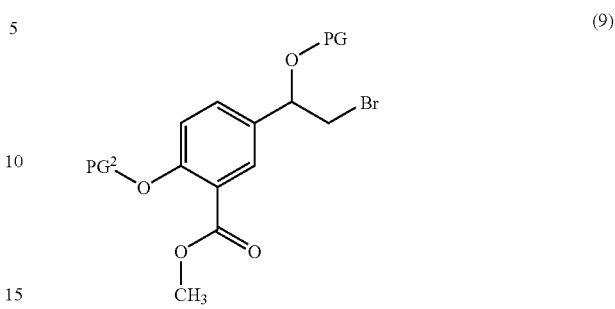

(9)

according to any method well-known to the one skilled in the art to prepare an alcohol from an ester, without modifying the rest of the molecule.

In a typical procedure, the ester of formula (9) is reduced with borane dimethylsulfide complex in tetrahydrofuran at reflux for a period of 2 hours.

The alcohol of formula (8) may be prepared as either the (R) or (S) enantiomer according to methods well described in the literature (Tetrahedron Letters 1994, 35(50), 9375).

When either $R^1$ or $R^2$ do not represent H, the amine of formula (7) may be prepared as either the (R) or (S) enantiomer from the corresponding protected amine of formula (10):

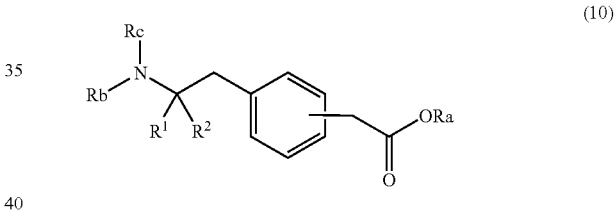

(10)

wherein the $CH_2-C(=O)ORa$ group is in the meta or para position and Ra is as previously defined and Rb and Rc represent any suitable substituents so that HNRbRc is a chiral amine (for example, Rb may be hydrogen and Rc may be α-methylbenzyl), provided that the bonds between N and Rb and N and Rc can be easily cleaved to give the free amine of formula (7) using standard methodology for cleaving nitrogen protecting groups, such as those found in the text book T. W. GREENE, Protective Groups in Organic Synthesis , A. Wiley-Interscience Publication, 1981.

In a typical procedure, the amine of formula (10) is treated with 20% palladium hydroxide on charcoal in the presence of an excess of ammonium formate in ethanol at room temperature for about 2 hours.

The amine of formula (10) may be prepared as a single diastereomer by reaction of an amine of formula HNRbRc with a ketone of formula (11):

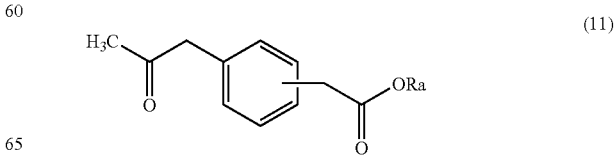

(11)

wherein the $CH_2-C(=O)ORa$ group is in the meta or para position and Ra, Rb and Rc are as previously defined.

In a typical procedure, the reaction of the ketone of formula (11) with the amine of formula HNRbRc leads to a chiral intermediate which is in turn reduced by a suitable reducing agent (e.g. sodium cyanoborohydride of formula $NaCNBH_3$ or sodium triacetoxyborohydride of formula $Na(OAc)_3BH$) optionally in the presence of a drying agent (e.g. molecular sieves, magnesium sulfate) and optionally in the presence of an acid catalyst (e.g. acetic acid) to give the amine of formula (10) as a mixture of diastereomers. The reaction is generally done in a solvent such as tetrahydrofuran or dichloromethane at a temperature comprised between 20° C. and 80° C. for 3 to 72 hours. The resulting product is then converted to the hydrochloride salt and selectively crystallised from a suitable solvent or mixture of solvents (e.g. isopropanol, ethanol, methanol, diisopropyl ether or diisopropyl ether/methanol) to give (10) as a single diastereomer.

In particular, the ketone of formula (11) may be prepared by palladium mediated coupling of an aryl halide of formula (12):

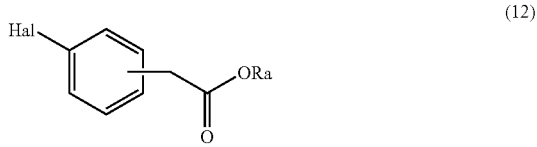

(12)

wherein the $CH_2-C(=O)ORa$ group is in the meta or para position and Ra is as previously defined and Hal represents an halogen atom, which includes, but is not limited to bromo and iodo, with an enolate or enolate equivalent.

In a typical procedure, the aryl halide of formula (12) is reacted with a tin enolate generated in-situ by treatment of isopropenyl acetate with tri-n-butyltin methoxide of formula $Bu_3SnOMe$ in the presence of a suitable palladium catalyst (palladium acetate/tri-ortho-tolylphosphine of formula $Pd(OAc)_2/P(o-Tol)_3$) in a non-polar solvent (e.g. toluene, benzene, hexane). Preferably, the reaction is carried out at a temperature comprised between 80° C. and 110° C. for 6 to 16 hours.

The aryl halide of formula (12) may be obtained by esterification of the corresponding acid of formula (13):

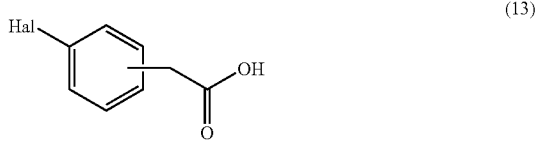

(13)

wherein the $CH_2-C(=O)OH$ group is in the meta or para position and Hal is as previously defined, according to any method well-known to the one skilled in the art to prepare an ester from an acid, without modifying the rest of the molecule.

In a typical procedure, the acid of formula (13) is reacted with an alcoholic solvent of formula RaOH, wherein Ra is as previously defined, in the presence of an acid such as hydrogen chloride at a temperature between 10° C. and 40° C. (room temperature) for 8 to 16 hours.

The acid of formula (13) is a commercial product.

The amine of formula (7), where $R^1$ and $R^2$ are both $C_1$-$C_4$ alkyl, may be prepared according to the following scheme:

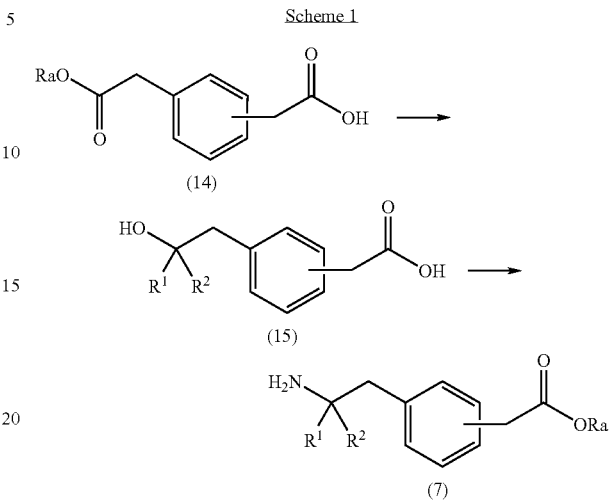

Scheme 1 wherein the $CH_2-C(=O)OH$ group is in the meta or para position and $R^1$, $R^2$ and Ra are as previously defined.

In a typical procedure, the ester of formula (14) is reacted with an "activated" alkyl (organometallic alkyl such as $R^2MgBr$, $R^2MgCl$ or $R^2Li$) to give the corresponding tertiary alcohol of formula (15) using the method described above.

The ester of formula (14) may be prepared from the corresponding diacid precursor (commercial) according to processes disclosed in International Journal of Peptide and Protein Research 1987, 29(3), 331.

Said tertiary alcohol of formula (15) is then treated with an alkyl nitrile (e.g. acetonitrile, chloroacetonitrile) in the presence of an acid (e.g. sulphuric acid, acetic acid) to give a protected intermediate which is in turn cleaved using standard methodology for cleaving nitrogen protecting group such as those mentioned in textbooks. The resulting amino acid is then esterified using the method described herein to give the amine of formula (7).

The compounds of formula (2), where $Q^1$ represents $-(CH_2)_n-$ and n represents 0, and $Q^2$ represents $-C(=O)NH-$, may alternatively be prepared by coupling an acid of formula (16):

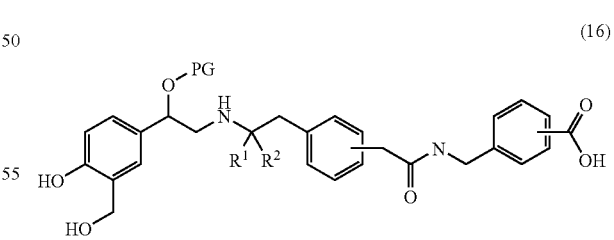

(16)

wherein the $CH_2-C(=O)NH-CH_2-Phenyl-COOH$ group is in the meta or para position and the Ra group is in the meta or para position with an amine of formula (17):

(17)

The acid of formula (16) is reacted with the amine of formula (17), with a conventional coupling agent (e.g. 1-(3-dimethylaminopropyl)-3-ethylcarbodiimide hydrochloride or N,N'-dicyclohexylcarbodiimide), optionally in the presence of a catalyst (e.g. 1-hydroxybenzotriazole hydrate or 1-hydroxy-7-azabenzotriazole), and optionally in the presence of a tertiary amine base (e.g. N-methylmorpholine, triethylamine or N-diisopropylethylamine). The reaction may be undertaken in a suitable solvent such as pyridine, N,N-dimethylformamide, tetrahydrofuran, dimethylsulfoxide, dichloromethane or ethyl acetate, and at temperature comprised between 10° C. and 40° C. (room temperature) for a period of 1-24 hours.

In a typical procedure, the acid of formula (16) is treated with the amine of formula (17) (1 eq), 1-(3-dimethylaminopropyl)-3-ethylcarbodiimide hydrochloride (1.1 eq), 1-hydroxybenzotriazole hydrate (1.1 eq) and triethylamine (3 eq) in N,N-dimethylformamide at room temperature for a period of 18 hours.

The amine of formula (17) is either commercially available or may be prepared by conventional methods well known to the one skilled in the art (e.g. reduction, oxidation, alkylation, protection, deprotection etc . . . ) from commercially available material.

The acid of formula (16) may be prepared from the corresponding ester of formula (18):

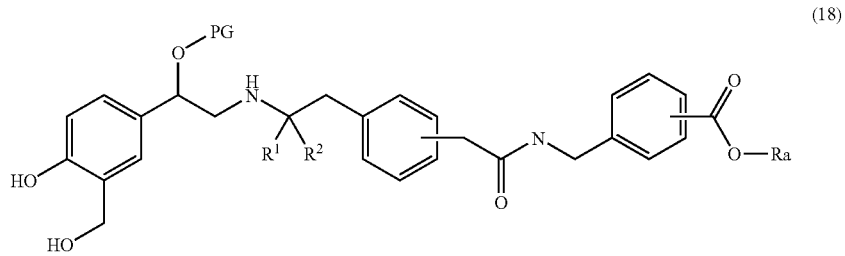

(18)

wherein the $CH_2$—$C(\!=\!O)NH$—$CH_2$-Phenyl-COORa group is in the meta or para position and Ra is a suitable acid protecting group, preferably a ($C_1$-$C_4$)alkyl group, which includes, but is not limited to, methyl and ethyl, according to any method well-known to the one skilled in the art to prepare an acid from an ester, without modifying the rest of the molecule. For example, the ester may be hydrolysed by treatment with aqueous acid or base (e.g. hydrogen chloride, potassium hydroxide, sodium hydroxide or lithium hydroxide), optionally in the presence of a solvent or mixture of solvents (e.g. water, 1,4-dioxan, tetrahydrofuran/water), at a temperature comprised between 20° C. and 100° C., for a period of 1 to 40 hours.

In a typical procedure the ester of formula (18) is treated with an excess of lithium hydroxide (2 eq) in aqueous tetrahydrofuran at room temperature for about 7 hours.

The ester of formula (18) may be prepared by coupling of the acid of formula (3) with the amine of formula (19):

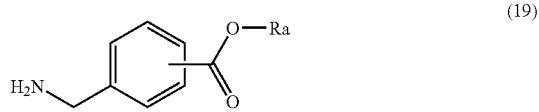

(19)

by analogy with the methods described previously for the the synthesis of the compound of formula (2).

The amine of formula (19) is commercially available.

The amine of formula (7), where $R^1$ and $R^2$ are both H, may be prepared according to the following scheme:

Scheme 3

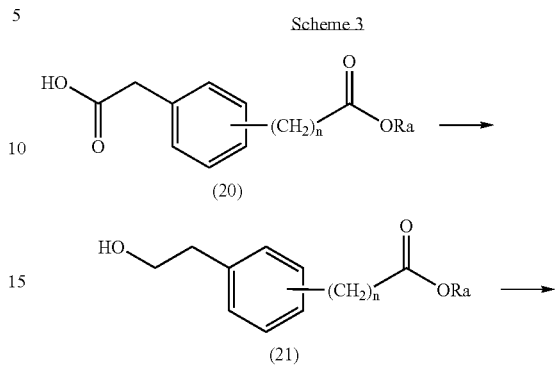

(20)

(21)

-continued

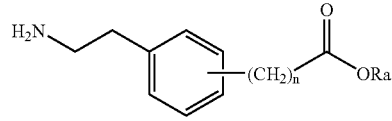

wherein $R^1$, $R^2$ and Ra are as previously defined.

In a typical procedure, the acid of formula (20) is preferentially reduced to the corresponding alcohol (21) in the presence of the ester. This may be performed by formation of the acyl imidazole or mixed anhydride and subsequent reduction with sodium borohydride or another suitable reducing agent.

Said primary alcohol of formula (21) is then converted into a leaving group such as mesylate, tosylate, bromide or iodide and displaced with appropriate amine nucleophile. The preferred nucleophile is azide ion which can then be reduced to the primary amine via hydrogenation or triphenylphosphine. Alternative nucleophiles could include ammonia or alkylamines such as benzylamine or allylamine and subsequent cleavage of the alkyl group to furnish the amine.

For some of the steps of the here above described process of preparation of the compounds of formula (1), it may be necessary to protect potential reactive functions that are not wished to react, and to cleave said protecting groups in consequence. In such a case, any compatible protecting radical can be used. In particular methods of protection and deprotection such as those described by T. W. GREENE (*Protective Groups in Organic Synthesis*, A. Wiley-Interscience Publication, 1981) or by P. J. Kocienski (*Protecting groups*, Georg Thieme Verlag, 1994), can be used.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Preferred compounds of formula (1) are those wherein $Q^1$ is $(CH_2)_n$ wherein n is 0 and $Q^2$ is —$SO_2NH$— or $C(=O)NH$—.

Other preferred compounds of formula (1) are those wherein $Q^1$ is $(CH_2)_n$ wherein n is 1 and $Q^2$ is —NH—C(=O)— or —NH—C(=O)—NH—.

In the above compounds of formula (1), the following substituents are further preferred:

Preferably, $R^1$ and $R^2$ are both $CH_3$.

Preferably, $R^1$ and $R^2$ are both H.

Preferably, $R^1$ is H and $R^2$ is $CH_3$.

More preferably, $R^1$ is H and $R^2$ is $CH_3$.

Preferably, $Q^3$ is a bond, —$CH_2$—, —$(CH_2)_2$—, —$C(CH_3)_2$—$CH_2$—, —$CH(CH_3)$—$CH(OH)$— or —$CH_2$—$CH(CH_3)$—.

Preferably $Q^4$ is

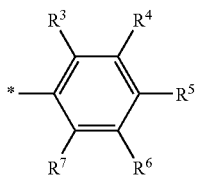

wherein $R^3$, $R^4$, $R^5$, $R^6$ and $R^7$ are selected from H, $C_1$-$C_4$ alkyl, phenyl, phenoxy $OR^8$, $SR^8$, halo, $CF_3$, $OCF_3$, $COOR^9$, $SO_2NR^8R^9$, $CONR^8R^9$, $NHR^8R^9$, $NHCOR^9$, and $CH_2$—$NHC(=O)NH$—$R^9$; and at least two of $R^3$ to $R^7$ represent H.

More preferably $Q^4$ is

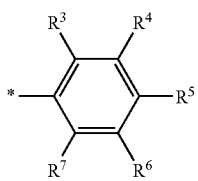

wherein $R^3$, $R^4$, $R^5$, $R^6$ and $R^7$ are selected from H, $C_1$-$C_4$ alkyl, phenyl, phenoxy $OR^8$, halo, $CF_3$ and $OCF_3$; and at least two of $R^3$ to $R^7$ represent H.

Particularly preferred are the compounds of the formula (1) as described in the Examples section hereafter, i.e.:

N-(4-tert-butylbenzyl)-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

N-(2-ethoxybenzyl)-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

4-{[({3-[(2R)-2-({(2R)-2-hydroxy-2-[4-hydroxy-3-(hydroxymethyl)phenyl]ethyl}amino)propyl]phenyl}acetyl)amino]methyl}-N-[4-(trifluoromethoxy)benzyl]benzamide;

N-(3,4-dichlorobenzyl)-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

N-[2-fluoro-5-(trifluoromethyl)benzyl]-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

N-[3,5-bis(trifluoromethyl)benzyl]-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

4-{[({3-[(2R)-2-({(2R)-2-hydroxy-2-[4-hydroxy-3-(hydroxymethyl)phenyl]ethyl}amino)propyl]phenyl}acetyl)amino]methyl}-N-(4-phenoxybenzyl)benzamide;

N-(1,1-dimethyl-2-phenylethyl)-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

N-[2-(4-ethylphenyl)ethyl]-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide N-[2-(4-chlorophenyl)ethyl]-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

N-[2-(4-ethoxyphenyl)ethyl]-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

N-[2-(1,1'-biphenyl-4-yl)ethyl]-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

4-{[({3-[(2R)-2-({(2R)-2-hydroxy-2-[4-hydroxy-3-(hydroxymethyl)phenyl]ethyl}amino)propyl]phenyl}acetyl)amino]methyl}-N-(4-hydroxy-3-methoxybenzyl)benzamide;

N-(1,1'-biphenyl-3-ylmethyl)-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

4-{[({3-[(2R)-2-({(2R)-2-hydroxy-2-[4-hydroxy-3-(hydroxymethyl)phenyl]ethyl}amino)propyl]phenyl}acetyl)amino]methyl}-N-[2-(3-methoxyphenyl)ethyl]benzamide;

N-[2-(3,4-dichlorophenyl)ethyl]-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

4-{[({3-[(2R)-2-({(2R)-2-hydroxy-2-[4-hydroxy-3-(hydroxymethyl)phenyl]ethyl}amino)propyl]phenyl}acetyl)amino]methyl}-N-[(2S)-2-phenylpropyl]benzamide;

4-{[({3-[(2R)-2-({(2R)-2-hydroxy-2-[4-hydroxy-3-(hydroxymethyl)phenyl]ethyl}amino)propyl]phenyl}acetyl)amino]methyl}-N-[(1R,2S)-2-hydroxy-1-methyl-2-phenylethyl]benzamide;

4-ethoxy-N-(4-{[({3-[(2R)-2-({(2R)-2-hydroxy-2-[4-hydroxy-3-(hydroxymethyl)phenyl]ethyl}amino)propyl]phenyl}acetyl)amino]methyl}benzyl)benzamide;

N-(4-{[({3-[(2R)-2-({(2R)-2-hydroxy-2-[4-hydroxy-3-(hydroxymethyl)phenyl]ethyl}amino)propyl]phenyl}acetyl)amino]methyl}benzyl)-1-naphthamide;

N-(4-{[({3-[(2R)-2-({(2R)-2-hydroxy-2-[4-hydroxy-3-(hydroxymethyl)phenyl]ethyl}amino)propyl]phenyl}acetyl)amino]methyl}benzyl)-2,2-diphenylacetamide;

N-(4-{[({3-[(2R)-2-({(2R)-2-hydroxy-2-[4-hydroxy-3-(hydroxymethyl)phenyl]ethyl}amino)propyl]phenyl}acetyl)amino]methyl}benzyl)-4-phenoxybenzamide;

N-{4-[(benzhydrylamino)methyl]benzyl}-2-{3-[(2R)-2-({(2R)-2-hydroxy-2-[4-hydroxy-3-(hydroxymethyl)phenyl]ethyl}amino)propyl]phenyl}acetamide;

N-{3-[(benzylamino)sulfonyl]benzyl}-2-{3-[(2R)-2-({(2R)-2-hydroxy-2-[4-hydroxy-3-(hydroxymethyl)phenyl]ethyl}amino)propyl]phenyl}acetamide;

2-{3-[(2R)-2-({(2R)-2-hydroxy-2-[4-hydroxy-3-(hydroxymethyl)phenyl]ethyl}amino)propyl]phenyl}-N-{4-[({[(3-phenoxybenzyl)amino]carbonyl}amino)methyl]benzyl}acetamide, and, N-(3,4-dimethoxybenzyl)-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide.

According to one aspect of the present invention, the compounds of formula (1) wherein the —CH$_2$—C(=O)NH-benzyl-Q$^1$-Q$^2$-Q$^3$-Q$^4$ group is in the meta position are generally preferred.

The compounds of formula (1) may also be optionally transformed into pharmaceutically acceptable salts. In particular, these pharmaceutically acceptable salts of the compounds of the formula (1) include the acid addition and the base salts (including disalts) thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, oxalate, palmitate, pamoate, phosphate/hydrogen, phosphate/phosphate dihydrogen, pyroglutamate, saccharate, stearate, succinate, tannate, D- and L-tartrate, 1-hydroxy-2-naphthoate tosylate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Stahl and Wermuth, Handbook of Pharmaceutical Salts: Properties, Selection, and Use, Wiley-VCH, Weinheim, Germany (2002).

Pharmaceutically acceptable salts of compounds of formula (1) may be prepared by one or more of three methods:
(i) by reacting the compound of formula (1) with the desired acid or base;
(ii) by removing an acid- or base-labile protecting group from a suitable precursor of the compound of formula (1) or by ring-opening a suitable cyclic precursor, for example, a lactone or lactam, using the desired acid or base; or
(iii) by converting one salt of the compound of formula (1) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol.

The term 'hydrate' is employed when said solvent is water. Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (1) include references to salts, solvates and complexes thereof and to solvates and complexes of salts thereof.

The compounds of the invention include compounds of formula (1) as hereinbefore defined, including all polymorphs and crystal habits thereof, prodrugs and isomers thereof (including optical, geometric and tautomeric isomers) as hereinafter defined and isotopically-labeled compounds of formula (1).

As indicated, so-called 'pro-drugs' of the compounds of formula (1) are also within the scope of the invention. Thus certain derivatives of compounds of formula (1) which may have little or no pharmacological activity themselves can, when administered into or onto the body, be converted into compounds of formula (1) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B Roche, American Pharmaceutical Association).

Prodrugs in accordance with the invention can, for example, be produced by replacing appropriate functionalities present in the compounds of formula (1) with certain moieties known to those skilled in the art as 'pro-moieties' as described, for example, in "Design of Prodrugs" by H. Bundgaard (Elsevier, 1985).

Some examples of prodrugs in accordance with the invention include:
(i) where the compound of formula (1) contains a carboxylic acid functionality (—COOH), an ester thereof, for example, a compound wherein the hydrogen of the carboxylic acid functionality of the compound of formula (1) is replaced by (C$_1$-C$_8$)alkyl;
(ii) where the compound of formula (1) contains an alcohol functionality (—OH), an ether thereof, for example, a compound wherein the hydrogen of the alcohol functionality of the compound of formula (1) is replaced by (C$_1$-C$_6$)alkanoyloxymethyl; and
(iii) where the compound of formula (1) contains a primary or secondary amino functionality (—NH$_2$ or —NHR where R≠H), an amide thereof, for example, a compound wherein, as the case may be, one or both hydrogens of the amino functionality of the compound of formula (1) is/are replaced by (C$_1$-C$_{10}$)alkanoyl.

Further examples of replacement groups in accordance with the foregoing examples and examples of other prodrug types may be found in the aforementioned references.

Moreover, certain compounds of formula (1) may themselves act as prodrugs of other compounds of formula (1).

Also included within the scope of the invention are metabolites of compounds of formula (1), that is, compounds formed in vivo upon administration of the drug. Some examples of metabolites in accordance with the invention include
(i) where the compound of formula (1) contains a methyl group, an hydroxymethyl derivative thereof (—$CH_3$→—$CH_2OH$):
(ii) where the compound of formula (1) contains an alkoxy group, an hydroxy derivative thereof (—OR→—OH);
(iii) where the compound of formula (1) contains a tertiary amino group, a secondary amino derivative thereof (—$NR^1R^2$→—$NHR^1$ or —$NHR^2$);
(iv) where the compound of formula (1) contains a secondary amino group, a primary derivative thereof (—$NHR^1$→—$NH_2$);
(v) where the compound of formula (1) contains a phenyl moiety, a phenol derivative thereof (-Ph→-PhOH); and
(vi) where the compound of formula (1) contains an amide group, a carboxylic acid derivative thereof (—$CONH_2$→COOH).

the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (1) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E. L. Eliel (Wiley, N.Y., 1994).

According to one aspect of the present invention, the (R,R)-stereoisomer of the formula below wherein $R^1$ is hydrogen and $R^2$ is $C_1$-$C_4$ alkyl, preferably methyl, and $Q^1$, $Q^2$, $Q^3$ and $Q^4$ are as defined above, is generally preferred:

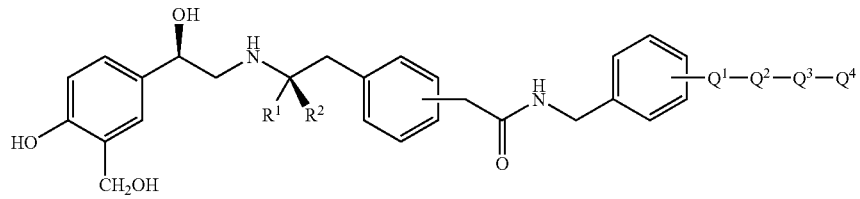

Compounds of formula (1) containing one or more asymmetric carbon atoms can exist as two or more stereoisomers. Where a compound of formula (1) contains an alkenyl or alkenylene group, geometric cis/trans (or Z/E) isomers are possible. Where the compound contains, for example, a keto or structural isomers are interconvertible via a low oxime group or an aromatic moiety, energy barrier, tautomeric isomerism ('tautomerism') can occur. This can take the form of proton tautomerism in compounds of formula (1) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (1), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or The present invention includes all pharmaceutically acceptable isotopically-labelled compounds of formula (1) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (1), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (1) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of formula (1), their pharmaceutically acceptable salts and/or derived forms, are valuable pharmaceutically active compounds, which are suitable for the therapy and prophylaxis of numerous disorders in which the β2 receptor is involved or in which agonism of this receptor may induce benefit, in particular the allergic and non-allergic airways diseases but also in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

The compounds of formula (1) and their pharmaceutically acceptable salts and derived forms as mentioned above can be administered according to the invention to animals, preferably to mammals, and in particular to humans, as pharmaceuticals for therapy and/or prophylaxis. They can be administered per se, in mixtures with one another or in the form of pharmaceutical preparations which as active constituent contain an efficacious dose of at least one compounds of formula (1), its pharmaceutically acceptable salts and/or derived forms, in addition to customary pharmaceutically innocuous excipients and/or additives.

The compounds of formula (1), their pharmaceutically acceptable salts and/or derived forms may be freeze-dried, spray-dried, or evaporatively dried to provide a solid plug, powder, or film of crystalline or amorphous material. Microwave or radio frequency drying may be used for this purpose.

The compounds of formula (1), their pharmaceutically acceptable salts and/or derived forms may be administered alone or in combination with other drugs and will generally be administered as a formulation in association with one or more pharmaceutically acceptable excipients. The term "excipient" is used herein to describe any ingredient other than the compound of the invention. The choice of excipient will to a large extent depend on the particular mode of administration.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (1), a film-forming polymer, a binder, a solvent, a humectant, a plasticiser, a stabiliser or emulsifier, a viscosity-modifying agent and a solvent. Some components of the formulation may perform more than one function.

The compound of formula (1) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (1) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (1) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLApoly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (1), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (1). The overall daily dose will typically be in the range 0.001 mg to 40 mg which may be administered in a single dose or, more usually, as divided doses throughout the day.

The compounds of formula (1) are particularly suitable for an administration by inhalation The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (1) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 5000 mg depending, of course, on the mode of administration. For example, an intravenous daily dose may only require from 0.001 mg to 40 mg. The total daily dose may be administered in single or divided doses_and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the compounds of the formula (1), or pharmaceutically acceptable salts, derived forms or compositions thereof, can also be used as a combination with one or more additional therapeutic agents to be co-administered to a patient to obtain some particularly desired therapeutic end result such as. the treatment of pathophysiologically-relevant disease processes including, but not limited to (i) bronchoconstriction, (ii) inflammation, (iii) allergy, (iv) tissue destruction, (v) signs and symptoms such as breathlessness, cough. The second and more additional therapeutic agents may also be a compound of formula (1), or a pharmaceutically acceptable salt, derived forms or compositions thereof, or one or more β2 agonists known in the art. More typically, the second and more therapeutic agents will be selected from a different class of therapeutic agents.

As used herein, the terms "co-administration", "co-administered" and "in combination with", referring to the compounds of formula (1) and one or more other therapeutic agents, is intended to mean, and does refer to and include the following:

simultaneous administration of such combination of compound(s) of formula (1) and therapeutic agent(s) to a patient in need of treatment, when such components are formulated together into a single dosage form which releases said components at substantially the same time to said patient, substantially simultaneous administration of such combination of compound(s) of formula (1) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (1) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (1) and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of formula (1), or pharmaceutically acceptable salts, derived forms or compositions thereof, include, but are by no means limited to:

(a) 5-Lipoxygenase (5-LO) inhibitors or 5-lipoxygenase activating protein (FLAP) antagonists,
(b) Leukotriene antagonists (LTRAs) including antagonists of $LTB_4$, $LTC_4$, $LTD_4$, and $LTE_4$,
(c) Histamine receptor antagonists including H1 and H3 antagonists,
(d) $\alpha_1$- and $\alpha_2$-adrenoceptor agonist vasoconstrictor sympathomimetic agents for decongestant use,
(e) muscarinic M3 receptor antagonists or anticholinergic agents,
(f) PDE inhibitors, e.g. PDE3, PDE4 and PDE5 inhibitors,
(g) Theophylline,
(h) Sodium cromoglycate,
(i) COX inhibitors both non-selective and selective COX-1 or COX-2 inhibitors (NSAIDs),
(j) Oral and inhaled glucocorticosteroids, such as DAGR (dissociated agonists of the corticoid receptor),
(k) Monoclonal antibodies active against endogenous inflammatory entities,
(l) Anti-tumor necrosis factor (anti-TNF-$\alpha$) agents,
(m) Adhesion molecule inhibitors including VLA-4 antagonists,
(n) Kinin-$B_1$- and $B_2$-receptor antagonists,
(o) Immunosuppressive agents,
(p) Inhibitors of matrix metalloproteases (MMPs),
(q) Tachykinin $NK_1$, $NK_2$ and $NK_3$ receptor antagonists,
(r) Elastase inhibitors,
(s) Adenosine A2a receptor agonists,
(t) Inhibitors of urokinase,
(u) Compounds that act on dopamine receptors, e.g. D2 agonists,
(v) Modulators of the NF$\kappa\beta$ pathway, e.g. IKK inhibitors,
(w) modulators of cytokine signalling pathways such as p38 MAP kinase, syk kinase or JAK kinase inhibitor,
(x) Agents that can be classed as mucolytics or anti-tussive,
(y) Antibiotics,
(z) HDAC inhibitors, and,
(aa) PI3 kinase inhibitors.

According to the present invention, combination of the compounds of formula (1) with:
H3 antagonists,
Muscarinic M3 receptor antagonists,
PDE4 inhibitors,
glucocorticosteroids,
Adenosine A2a receptor agonists,
Modulators of cytokine signalling pathways such as p38 MAP kinase or syk kinase, or,
Leukotriene antagonists (LTRAs) including antagonists of $LTB_4$, $LTC_4$, $LTD_4$, and $LTE_4$, are preferred.

According to the present invention, combination of the compounds of formula (1) with:
glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, ciclesonide, and mometasone furoate, or
muscarinic M3 receptor antagonists or anticholinergic agents including in particular ipratropium salts, namely bromide, tiotropium salts, namely bromide, oxitropium salts, namely bromide, perenzepine, and telenzepine, are further preferred.

It is to be appreciated that all references herein to treatment include curative, palliative and prophylactic treatment. The description, which follows, concerns the therapeutic applications to which the compounds of formula (1) may be put.

The compounds of formula (1) have the ability to interact with the $\beta$2 receptor and thereby have a wide range of therapeutic applications, as described further below, because of the essential role which the $\beta$2 receptor plays in the physiology of all mammals.

Therefore, a further aspect of the present invention relates to the compounds of formula (1), or pharmaceutically acceptable salts, derived forms or compositions thereof, for use in the treatment of diseases, disorders, and conditions in which the $\beta$2 receptor is involved. More specifically, the present invention also concerns the compounds of formula (1), or pharmaceutically acceptable salts, derived forms or compositions thereof, for use in the treatment of diseases, disorders, and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, *staphylococcus* or streptococcal bronchitis and vesicular bronchitis, acute lung injury, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

A still further aspect of the present invention also relates to the use of the compounds of formula (1), or pharmaceutically acceptable salts, derived forms or compositions thereof, for the manufacture of a drug having a β2 agonist activity. In particular, the present inventions concerns the use of the compounds of formula (1), or pharmaceutically acceptable salts, derived forms or compositions thereof, for the manufacture of a drug for the treatment of β2-mediated diseases and/or conditions, in particular the diseases and/or conditions listed above.

As a consequence, the present invention provides a particularly interesting method to treat a mammal, including a human being, with an effective amount of a compound of formula (1), or a pharmaceutically acceptable salt, derived form or composition thereof. More precisely, the present invention provides a particularly interesting method for the treatment of a β2-mediated diseases and/or conditions in a mammal, including a human being, in particular the diseases and/or conditions listed above, comprising admidministering said mammal with an effective amount of a compound of formula (1), its pharmaceutically acceptable salts and/or derived forms.

The following examples illustrate the preparation of the compounds of the formula (1):

EXAMPLES 1 to 12

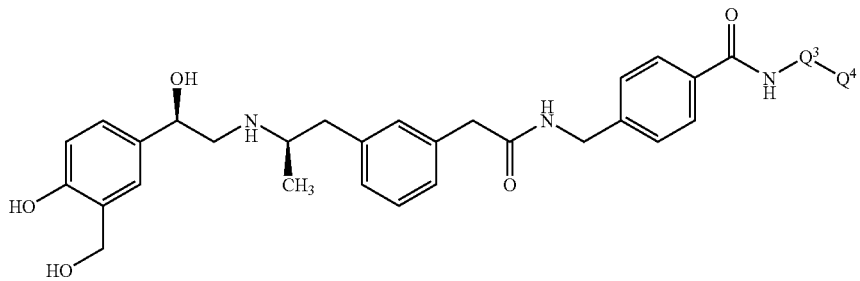

A solution of ammonium fluoride in water (15 eq, 20 mg·ml$^{-1}$) was added to a solution of the protected compound from preparations 37, 39-43, 45, 46,48, 49, 52 and 54 (1 eq) in methanol (45-100 ml·mmol$^{-1}$) and the reaction stirred at 40° C. for 18 hours. The reaction mixture was evaporated under reduced pressure and the residue purified by column chromatography using a Biotage® silica gel cartridge using dichloromethane:methanol:0.88 ammonia (97:3:0.3 to 93:7:0.7) as eluant. The product was triturated with ether to afford the title compound as a solid.

| Ex. No | Q³—Q⁴ | Data |
|---|---|---|
| 1 | ![structure with C(CH3)3 group on benzyl] | $^1$H NMR(CD$_3$OD, 400 MHz) δ: 1.06(d, 3H), 1.30(s, 9H), 2.56-2.61(m, 1H), 2.69-2.74(m, 2H), 2.84-2.89(m, 1H), 2.92-2.98(m, 1H), 3.52(s, 2H), 4.40(s, 2H), 4.51(s, 2H), 4.57-4.65 (m, 3H), 6.69(d, 1H), 7.01(d, 2H), 7.08(s, 1H), 7.14(d, 1H), 7.18-7.22(m, 2H), 7.25(d, 2H), 7.30(d, 2H), 7.36(d, 2H), 7.77(d, 2H). LRMS: m/z ES$^+$ 638[MH$^+$] Microanalysis found: C, 70.36; H, 7.43; N, 6.25. C$_{39}$H$_{47}$N$_3$O$_5$ + H$_2$O requires C, 70.36; H, 7.59; N, 6.31%. |
| 2 | ![structure with H3C-O-phenyl benzyl] | $^1$H NMR(CD$_3$OD, 400 MHz) δ: 1.06(d, 3H), 1.38-1.42(t, 3H), 2.55-2.60(m, 1H), 2.68-2.73 (m, 2H), 2.83-2.88(m, 1H), 2.92-2.97(m, 1H), 3.52(s, 2H), 4.06-4.11(q, 2H), 4.40(s, 2H), 4.56(s, 2H), 4.57-4.62(m, 3H), 6.68(d, |

-continued

| Ex. No | Q³—Q⁴ | Data |
|---|---|---|
| | | 1H), 6.85-6.89(m, 1H), 6.93(d, 1H), 7.01(m, 2H), 7.08(s, 1H), 7.13(d, 1H), 7.18-7.24(m, 4H), 7.30(d, 2H), 7.76(d, 2H).<br>LRMS: m/z ES⁺ 626[MH⁺]<br>Microanalysis found: C, 69.12; H, 6.86; N, 6.52. $C_{37}H_{43}N_3O_6$ + 0.95 $H_2O$ requires C, 69.12; H, 7.05; N, 6.53%. |
| 3 | 4-(trifluoromethoxy)benzyl | $^1$H NMR(CD$_3$OD, 400 MHz) δ: 1.05(d, 3H), 2.53-2.62(m, 1H), 2.67-2.72(m, 2H), 2.83-2.88(m, 1H), 2.89-2.96(m, 1H), 3.51(s, 2H), 4.40(s, 2H), 4.56(s, 2H), 4.57-4.63(m, 3H), 6.68(d, 1H), 7.00(d, 2H), 7.07(s, 1H), 7.13(d, 1H), 7.17-7.23(m, 4H), 7.31(d, 2H), 7.42(d, 2H), 7.77(d, 2H).<br>LRMS: m/z ES⁺ 666[MH⁺]<br>Microanalysis found: C, 62.95; H, 5.69; N, 6.07. $C_{36}H_{38}F_3N_3O_6$ + 1.15 $H_2O$ requires C, 62.99; H, 5.92; N, 6.12%. |
| 4 | 3,4-dichlorobenzyl | $^1$H NMR(CD$_3$OD, 400 MHz) δ: 1.06(d, 3H), 2.56-2.63(m, 1H), 2.69-2.79(m, 2H), 2.83-2.89(m, 1H), 2.95-3.03(m, 1H), 3.52(s, 2H), 4.40(s, 2H), 4.50(s, 2H), 4.60-4.66(m, 3H), 6.68(d, 1H), 7.01(d, 2H), 7.08(s, 1H), 7.14(d, 1H), 7.18-7.27(m, 3H), 7.31(d, 2H), 7.45-7.48(m, 2H), 7.77(d, 2H).<br>LRMS: m/z ES⁺ 650[MH⁺]<br>Microanalysis found: C, 61.52; H, 5.68; N, 6.02. $C_{35}H_{37}Cl_2N_3O_5$ + 1.7 $H_2O$ requires C, 61.71; H, 5.98; N, 6.17%. |
| 5 | 2-fluoro-5-(trifluoromethyl)benzyl | $^1$H NMR(CD$_3$OD, 400 MHz) δ: 1.06(d, 3H), 2.55-2.60(m, 1H), 2.65-2.73(m, 2H), 2.83-2.96(m, 2H), 3.52(s, 2H), 4.40(s, 2H), 4.55-4.63(m, 3H), 4.64(s, 2H), 6.68(d, 1H), 7.01(d, 2H), 7.08(s, 1H), 7.13(d, 1H), 7.19(d, 2H), 7.27-7.33(m, 3H), 7.59-7.66(m, 1H), 7.70(d, 1H), 7.78(d, 2H).<br>LRMS: m/z ES⁺ 668[MH⁺] |
| 6 | 3,5-bis(trifluoromethyl)benzyl | $^1$H NMR(CD$_3$OD, 400 MHz) δ: 1.06(d, 3H), 2.55-2.60(m, 1H), 2.65-2.72(m, 2H), 2.84-2.89(m, 1H), 2.92-2.97(m, 1H), 3.52(s, 2H), 4.40(s, 2H), 4.55-4.62(m, 3H), 4.68(s, 2H), 6.68(d, 1H), 7.01(d, 2H), 7.08(s, 1H), 7.13(d, 1H), 7.18(m, 2H), 7.32(d, 2H), 7.79(d, 2H), 7.85(s, 1H), 7.93(s, 2H).<br>LRMS: m/z ES⁺ 718[MH⁺]<br>Microanalysis found: C, 60.66; H, 5.35; N, 5.68. $C_{37}H_{37}F_6N_3O_5$ + 0.8 $H_2O$ requires C, 60.70; H, 5.31; N, 5.74%. |
| 7 | 4-phenoxybenzyl | $^1$H NMR(CD$_3$OD, 400 MHz) δ: 1.06(d, 3H), 2.58(m, 1H), 2.66-2.74(m, 2H), 2.82-2.88(m, 1H), 2.90-2.96(m, 1H), 3.51(s, 2H), 4.39(s, 2H), 4.52(s, 2H), 4.57-4.64(m, 3H), 6.68(d, 1H), 6.92-6.96(m, 4H), 7.00(d, 2H), 7.07(m, 2H), 7.12(d, 1H), 7.19(m, 2H), 7.29-7.35(m, 6H), 7.77(d, 2H).<br>LRMS: m/z ES⁺ 696[MNa⁺]<br>Microanalysis found: C, 70.59; H, 6.41; N, 6.04. $C_{41}H_{43}N_3O_6$ + 1.3 $H_2O$ requires C, 70.63; H, 6.59; N, 6.03%. |
| 8 | 2,2-dimethyl-3-phenylpropyl | $^1$H NMR(CD$_3$OD, 400 MHz) δ: 1.06(d, 3H), 1.40(s, 6H), 2.56-2.62(m, 1H), 2.67-2.73(m, 2H), 2.84-2.89(m, 1H), 2.92-2.97(m, 1H), 3.16(s, 2H), 3.51(s, 2H), 4.39(s, 2H), 4.59(m, 3H), 6.68(d, 1H), 7.01(m, 2H), 7.08(s, 1H), 7.12-7.21(m, 8H), 7.25(d, 2H), 7.60(d, 2H).<br>LRMS: m/z ES⁺ 646[MNa⁺]<br>Microanalysis found: C, 70.15; H, 7.31; N, 6.42. $C_{38}H_{45}N_3O_5$ + 1.5 $H_2O$ requires C, 70.13; H, 7.43; N, 6.46%. |

| Ex. No | Q³—Q⁴ | Data |
|---|---|---|
| 9 | 4-ethyl-benzyl (CH₂-C₆H₄-CH₃) | ¹H NMR(CD₃OD, 400 MHz) δ: 1.06(d, 3H), 1.16-1.23(m, 3H), 2.55-2.62(m, 3H), 2.66-2.74 (m, 2H), 2.82-2.90(m, 3H), 2.93(m, 1H), 3.47-3.56(m, 4H), 4.39(s, 2H), 4.57-4.64(m, 3H), 6.69(d, 1H), 7.01(d, 2H), 7.08-7.18(m, 6H), 7.20(m, 2H), 7.28(d, 2H), 7.69(d, 2H). LRMS: m/z ES⁺ 646[MNa⁺] Microanalysis found: C, 71.03; H, 7.21; N, 6.49. $C_{38}H_{45}N_3O_5$ + 1.05 $H_2O$ requires C, 71.01; H, 7.39; N, 6.54%. |
| 10 | 4-chloro-benzyl | ¹H NMR(CD₃OD, 400 MHz) δ: 1.06(d, 3H), 2.56-2.61(m, 1H), 2.67-2.74(m, 2H), 2.82-2.90 (m, 3H), 2.92-2.99(m, 1H), 3.46-3.58(m, 4H), 4.39(s, 2H), 4.57-4.64(m, 3H), 6.69(d, 1H), 7.02(m, 2H), 7.08(s, 1H), 7.13(d, 1H), 7.18-7.32(m, 8H), 7.68(d, 2H). LRMS: m/z ES⁺ 652[MNa⁺] Microanalysis found: C, 66.04; H, 6.47; N, 6.41. $C_{36}H_{40}ClN_3O_5$ + 1.35 $H_2O$ requires C, 66.06; H, 6.58; N, 6.42%. |
| 11 | 4-(2-ethoxyethoxy)-benzyl | ¹H NMR(CD₃OD, 400 MHz) δ: 1.06(d, 3H), 1.35(t, 3H), 2.54-2.60(m, 1H), 2.67-2.72(m, 2H), 2.80-2.95(m, 4H), 3.45-3.55(m, 4H), 3.95-4.01(q, 2H), 4.39(s, 2H), 4.57-4.63(m, 3H), 6.68(d, 1H), 6.81(d, 2H), 7.01(d, 2H), 7.08(s, 1H), 7.12(m, 3H), 7.17-7.22(m, 2H), 7.28(d, 2H), 7.68(d, 2H). LRMS: m/z ES⁺ 640[MH⁺] |
| 12 | biphenyl-4-ylmethyl | ¹H NMR(CD₃OD, 400 MHz) δ: 1.05(d, 3H), 2.54-2.59(m, 1H), 2.66-2.71(m, 2H), 2.86-2.96 (m, 4H), 3.51(s, 2H), 3.61(t, 2H), 4.39(s, 2H), 4.57-4.61(m, 3H), 6.68(d, 1H), 7.00(d, 2H), 7.07(s, 1H), 7.12(d, 1H), 7.16-7.20(m, 2H), 7.27-7.32(m, 5H), 7.38-7.42(m, 2H), 7.52-7.58(m, 4H), 7.70(d, 2H). LRMS: m/z ES⁺ 694[MNa⁺] Microanalysis found: C, 72.51; H, 6.75; N, 6.25. $C_{42}H_{45}N_3O_5$ + 1.35 $H_2O$ requires C, 72.46; H, 6.91; N, 6.04%. |

EXAMPLES 13 TO 18

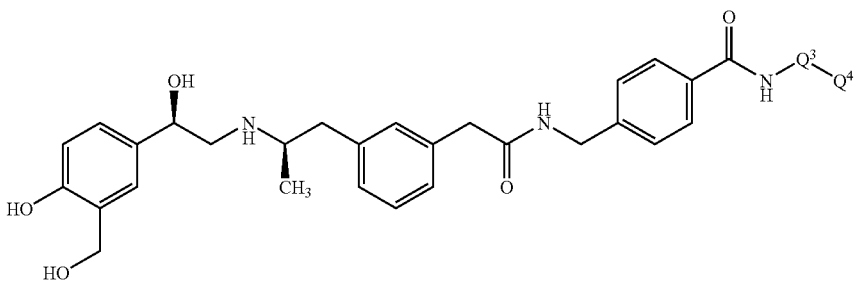

Ammonium fluoride (10-15 eq) was added to a solution of the protected compound from preparations 38, 44, 51, 50, 47 and 53 (1 eq) in methanol (40-44 ml·mmol⁻¹) and water (17-25 ml·mmol⁻¹) and the reaction stirred at 40° C. for 18 hours. The reaction mixture was evaporated under reduced pressure and the residue purified by column chromatography on silica gel using dichloromethane:methanol:0.88 ammonia (95:5:0.5 to 90:10:1) as eluant. The product was triturated with ether or pentane to afford the title compound as a solid.

| Ex. No | Q³—Q⁴ | Data |
|---|---|---|
| 13 | 4-OH, 3-OCH₃ benzyl | ¹H NMR(CD₃OD, 400 MHz) δ: 1.06-1.19 (m, 3H), 2.62-2.68(m, 1H), 2.89(m, 2H), 3.13-3.24(m, 1H), 3.54(s, 3H), 3.82(s, 3H), 4.40(s, 2H), 4.45(s, 2H), 4.63(s, 2H), 4.69-4.76(m, 1H), 6.73-6.79 (m, 3H), 6.93(s, 1H), 7.07-7.18(m, 4H), 7.23-7.31(m, 4H), 7.76(d, 2H). LRMS: m/z ES⁺ 628[MH⁺] |
| 14^A | 3-phenyl benzyl (biphenyl) | ¹H NMR(CD₃OD, 400 MHz) δ: 1.04(d, 3H), 2.56-2.60(dd, 1H), 2.65-2.63(m, 2H), 2.82-2.98(m, 2H), 3.53(s, 2H), 4.40(s, 2H), 4.60(m, 5H), 6.69(d, 1H), 7.00(d, 2H), 7.07(s, 1H), 7.15(d, 1H), 7.20(m, 2H), 7.30(m, 4H), 7.40(m, 3H), 7.50(d, 1H), 7.58(m, 3H), 7.80(d, 2H). LRMS m/z ES⁺ 658[MH⁺] Microanalysis found: C, 72.90; H, 6.69; N, 6.09. C₄₁H₄₃N₃O₅ + H₂O requires C, 72.87; H, 6.71; N, 6.22%. |
| 15 | 3-(OCH₃)phenethyl | ¹H NMR(CD₃OD, 400 MHz) δ: 1.07(d, 3H), 2.56-2.62(dd, 1H), 2.73(dd, 2H), 2.85-2.91(m, 3H), 2.95-3.00(m, 1H), 3.52-3.58(m, 4H), 3.74(s, 3H), 4.40(s, 2H), 4.61(m, 3H), 6.70(d, 1H), 6.76(d, 1H), 6.81(d, 2H), 7.03(d, 2H), 7.09-7.22 (m, 5H), 7.29(d, 2H), 7.69(d, 2H). LRMS: m/z ES⁺ 626[MH⁺] Microanalysis found: C, 69.25; H, 7.04; N, 6.52. C₃₇H₄₃N₃O₆ + 0.9 H₂O requires C, 69.22; H, 7.03; N, 6.55%. |
| 16^A, B | 3,4-dichloro phenethyl | ¹H NMR(CD₃OD, 400 MHz) δ: 1.08(d, 3H), 2.56-2.63(m, 1H), 2.72-2.77(m, 1H), 2.88(m, 4H), 2.95-3.01(m, 1H), 3.52(s, 2H), 3.56(t, 2H), 4.40(s, 2H), 4.62(m, 3H), 6.70(d, 1H), 7.02(m, 2H), 7.14(m, 1H), 7.19(m, 1H), 7.22(m, 3H), 7.28(d, 2H), 7.41(d, 2H), 7.68(d, 2H). LRMS: m/z ES⁺ 686[MNa⁺] |
| 17 | (R)-α-methylphenethyl | ¹H NMR(CD₃OD, 400 MHz) δ: 1.01(d, 3H), 1.25(d, 3H), 2.50-2.55(m, 1H), 2.62-2.67(m, 2H), 2.78-2.90(m, 2H), 3.03-3.09(m, 1H), 3.39-3.50(m, 4H), 4.33(s, 2H), 4.52-4.61(m, 3H), 6.64(d, 1H), 6.95(d, 2H), 7.02(s, 2H), 7.07-7.30 (m, 9H), 7.56(d, 2H). LRMS: m/z ES⁺ 610[MH⁺] Microanalysis found: C, 70.90; H, 7.13; N, 6.53. C₃₇H₄₃N₃O₅ + 0.95 H₂O requires C, 70.89; H, 7.22; N, 6.70%. |
| 18 | (αR,βS)-α-methyl-β-hydroxy phenethyl | ¹H NMR(CD₃OD, 400 MHz) δ: 1.07(d, 3H), 1.19(d, 3H), 2.57-2.68(dd, 1H), 2.71-2.76(m, 2H), 2.85-2.91(m, 2H), 2.96-3.01(m, 1H), 3.52(s, 2H), 4.29-4.25 (m, 1H), 4.38(s, 2H), 4.62(m, 3H), 4.78(d, 1H), 6.70(d, 1H), 7.02(d, 2H), 7.09(s, 1H), 7.13(d, 1H), 7.19-7.32(m, 7H), 7.41(d, 2H), 7.63(d, 2H). LRMS: m/z ES⁺ 626[MH⁺] Microanalysis found: C, 68.04; H, 7.11; N, 6.43. C₃₇H₄₃N₃O₆ + 1.25 H₂O requires C, 68.55; H, 7.09; N, 6.48%. |

A-tlc analysis after 18 hours, showed starting material remaining, so additional ammonium fluoride (5-6 eq) was added and the reaction stirred for a further 18 hours at 40° C.

B-compound purified using a Biotage® silica gel cartridge and dichloromethane:methanol:0.88 ammonia (100:0:0 to 95:5:0.5) as eluant.

EXAMPLES 19 TO 23

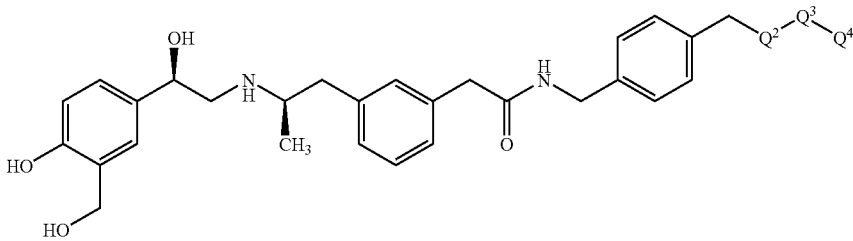

The compounds of the general formula shown above, were prepared from the compounds of preparations 31, 33, 32, 34 and 30, following the procedure described for examples 13 to 18.

| Ex. No | $Q^2$—$Q^3$—$Q^4$ | Data |
|---|---|---|
| 19A | [4-ethoxybenzamide group] | $^1$H NMR(CD$_3$OD, 400 MHz) δ: 1.05(d, 3H), 1.40(t, 3H), 2.54-2.59(dd, 1H), 2.67-2.72 (dd, 2H), 2.83-2.97(m, 2H), 3.49(s, 2H), 4.05-4.11(q, 2H), 4.33(s, 2H), 4.51(s, 2H), 4.57-4.63(m, 3H), 6.69(d, 1H), 6.93-7.02(m, 4H), 7.07(s, 1H), 7.11(d, 1H), 7.16-7.23(m, 4H), 7.26(d, 2H), 7.79(d, 2H). LRMS: m/z ES$^+$ 626[MH]$^+$ Microanalysis found: C, 68.69; H, 7.01; N, 6.54. C$_{37}$H$_{43}$N$_3$O$_6$ + 1.25 H$_2$O requires C, 68.55; H, 7.07; N, 6.48%. |
| 20A | [naphthalene-1-carboxamide] | $^1$H NMR(CD$_3$OD, 400 MHz) δ: 1.05(d, 3H), 2.54-2.62(m, 1H), 2.69-2.74(m, 2H), 2.83-2.89(m, 1H), 2.93-2.98(m, 1H), 3.51(s, 2H), 4.36(s, 2H), 4.58-4.63(m, 5H), 6.69(d, 1H), 7.00(d, 2H), 7.08(s, 1H), 7.13(d, 1H), 7.17-7.25(m, 4H), 7.37(d, 2H), 7.48-7.53(m, 3H), 7.60(d, 1H), 7.91(m, 1H), 7.96(d, 1H), 8.15(m, 1H). LRMS: m/z ES$^+$ 632[MH]$^+$ Microanalysis found: C, 72.16; H, 6.82; N, 6.20. C$_{39}$H$_{41}$N$_3$O$_5$ + 0.95 H$_2$O requires C, 72.19; H, 6.66; N, 6.48%. |
| 21 | [2,2-diphenylacetamide] | $^1$H NMR(CD$_3$OD, 400 MHz) δ: 1.05(d, 3H), 2.53-2.64(m, 1H), 2.64-2.74(m, 2H), 2.82-2.97(m, 2H), 3.48(s, 2H), 4.31(s, 2H), 4.37(s, 2H), 4.60(m, 3H), 4.98(s, 1H), 6.69(d, 1H), 7.00(d, 2H), 7.05(s, 1H), 7.10-7.32(m, 17H). LRMS: m/z ES$^+$ 672[MH$^+$] [α]$_D$ = −10.40(c = 0.10, MeOH) |
| 22A | [4-phenoxybenzamide] | $^1$H NMR(CD$_3$OD, 400 MHz) δ: 1.05(d, 3H), 2.53-2.63(m, 1H), 2.68-2.72(m, 2H), 2.84-2.97(m, 2H), 3.49(s, 2H), 4.33(s, 2H), 4.52(s, 2H), 4.61(s, 3H), 6.69(d, 1H), 6.98-7.13(m, 8H), 7.19(m, 5H), 7.27(d, 2H), 7.40(m, 2H), 7.83(d, 2H). LRMS: m/z ES$^+$ 674[MH$^+$] Microanalysis found: C, 71.16; H, 6.58; N, 5.94. C$_{41}$H$_{43}$N$_3$O$_6$ + 1.0 H$_2$O requires C, 71.18; H, 6.56; N, 6.07%. [α]$_D$ = −17.4(c = 0.12, MeOH) |

| Ex. No | Q²—Q³—Q⁴ | Data |
|---|---|---|
| 23^A | 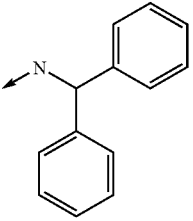 | ¹H NMR(CD₃OD, 400 MHz) δ: 1.06(d, 3H), 2.55-2.61(dd, 1H), 2.68-2.79(m, 2H), 2.84-2.90(m, 1H), 2.93-2.98(m, 1H), 3.51(s, 2H), 3.65(s, 2H), 4.34(s, 2H), 4.58-4.63(m, 3H), 4.76(s, 1H), 6.69(d, 1H), 7.01(d, 2H), 7.09(s, 1H), 7.13(d, 1H), 7.17-7.23(m, 8H), 7.26-7.30(m, 4H), 7.36(m, 4H). LRMS: m/z ES⁺ 644[MH⁺] Microanalysis found: C, 74.55; H, 7.12; N, 6.45. C₄₁H₄₅N₃O₄ + 0.85 H₂O requires C, 74.71; H, 7.14; N, 6.37%. [α]_D = −21.10(c = 0.11, MeOH) |

A-tlc analysis after 18 hours, showed starting material remaining, so additional ammonium fluoride (5-6 eq) was added and the reaction stirred for a further 18 hours at 40° C.

EXAMPLE 24

N-{3-[(Benzylamino)sulfonyl]benzyl}-2-{3-[(2R)-2-({(2R)-2-hydroxy-2-[4-hydroxy-3-(hydroxymethyl) phenyl]ethyl}amino)propyl]phenyl}acetamide

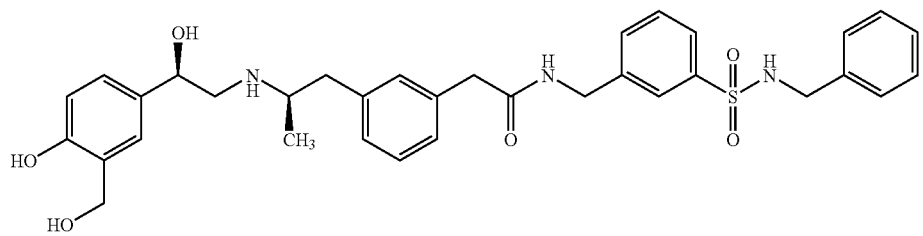

Ammonium fluoride (134 mg, 3.61 mmol) was added to a solution of the compound from preparation 36 (132 mg, 0.18 mmol) in water (4 ml) and methanol (7 ml) and the reaction stirred at 40° C. for 18 hours. The solvent was removed in vacuo and the residue was purified by column chromatography on silica gel using dichloromethane:methanol:0.88 ammonia (93:7:0.5) to give a colourless gum. This was triturated with ether and the mixture evaporated under reduced pressure to afford the title compound as a white solid, 55 mg.

¹H NMR (CD₃OD, 400 MHz), δ: 1.06 (d, 3H), 2.55-2.60 (dd, 1H), 2.67-2.73 (m, 2H), 2.84-2.89 (m, 1H), 2.93-2.98 (m, 1H), 3.53 (s, 2H), 3.98 (s, 2H), 4.40 (s, 2H), 4.59-4.63 (m, 3H), 6.69 (d, 1H), 6.98-7.03 (m, 2H), 7.08 (s, 1H), 7.13-7.24 (m, 8H), 7.44 (d, 2H), 6.67-7.72 (m, 2H). LRMS: m/z ES⁺ 618 [MH⁺] Microanalysis found: C, 64.50; H, 6.47; N, 6.54. C₃₄H₃₉N₃O₆S+0.85H₂O requires C, 64.51; H, 6.48; N, 6.64%.

EXAMPLE 25

2-{3-[(2R)-2-({(2R)-2-Hydroxy-2-[4-hydroxy-3-(hydroxymethyl)phenyl]ethyl}amino)propyl]phenyl}-N-{4-[({[(3-phenoxybenzyl)amino] carbonyl}amino)methyl]benzyl}acetamide

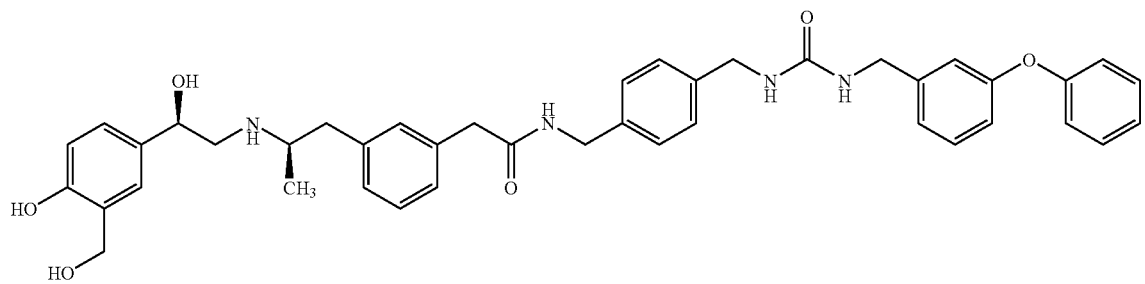

The title compound was prepared from the compound from preparation 55 (157 mg, 0.192 mmol) as a white solid in 54% yield, following the procedure described in example above.

$^1$H NMR (CD$_3$OD, 400 MHz), δ: 1.05 (d, 3H), 2.52-2.57 (dd, 1H), 2.65-2.71 (m, 2H), 2.82-2.93 (m, 2H), 3.48 (s, 2H), 4.22-4.30 (m, 6H), 4.61 (s, 3H), 6.66-6.70 (d, 1H), 6.83 (d, 1H), 6.92-7.33 (m, 18H). LRMS: m/z ES$^+$ 703 [MH$^+$] Microanalysis found: C, 70.04; H, 6.81; N, 7.82. C$_{42}$H$_{46}$N$_4$O$_6$+0.95H$_2$O requires C, 70.07; H, 6.71; N, 7.78%.

EXAMPLE 26

N-(3,4-Dimethoxybenzyl)-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide

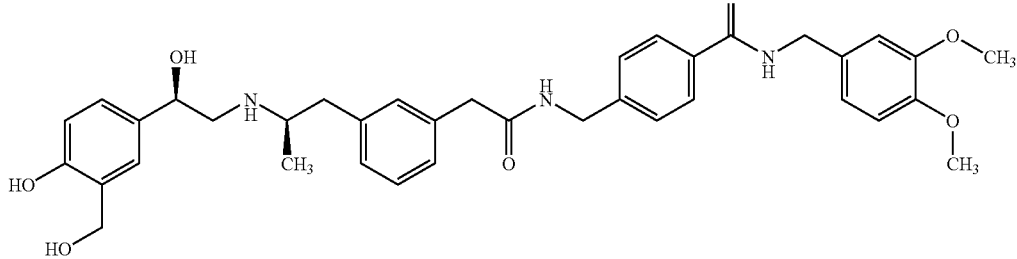

A solution of the compound from preparation 35 (170 mg, 0.23 mmol) in tetrahydrofuran (2 ml), water (2 ml) and acetic acid (6 ml) was stirred at 65° C. for 18 hours, and a further 72 hours at room temperature. The reaction mixture was evaporated under reduced pressure and the residue purified by column chromatography on silica gel using an elution gradient of dichloromethane:methanol:0.88 ammonia (95:5:0.5 to 90:10:1). The resulting gum was triturated with ether to afford the title compound as a white solid, 61 mg.

$^1$H NMR (CD$_3$OD, 400 MHz), δ: 1.06 (d, 3H), 2.55-2.61 (dd, 1H), 2.66-2.75 (m, 2H), 2.82-2.98 (m, 2H), 3.52 (s, 2H), 3.80 (s, 6H), 4.40 (s, 2H), 4.48 (s, 2H), 4.61 (m, 3H), 6.69 (d, 1H), 6.89 (s, 2H), 6.96 (s, 1H), 7.01 (d, 2H), 7.08 (s, 1H), 7.13 (m, 1H), 7.19 (m, 2H), 7.30 (d, 2H), 7.77 (d, 2H). LRMS: m/z ES$^+$ 618 [MH$^+$] [α]$_D$=-17.20 (c=0.10, MeOH).

Preparation 1

Methyl 2-(benzyloxy)-5-((1R)-2-bromo-1-{[tert-butyl(dimethyl)silyl]oxy}ethyl)benzoate A solution of methyl 2-(benzyloxy)-5-[(1R)-2-bromo-1-hydroxyethyl]benzoate (Tett. Lett. 1994, 35(50), 9375) (71.05 g, 195 mmol), imidazole (18.52 g, 272 mmol), tert-butyldimethylsilyl chloride (32.23 g, 214 mmol) and 4-dimethylaminopyridine (0.44 g, 3.6 mmol) in N,N-dimethylformamide (270 ml) was stirred at room temperature under a nitrogen atmosphere for 24 hours. The solvent was removed in vacuo and the residue partitioned between ethyl acetate (500 ml) and water (500 ml). The organic phase was separated and washed with 2N hydrochloric acid (2×500 ml), saturated aqueous sodium bicarbonate (2×500 ml) saturated sodium chloride (500 ml), dried (magnesium sulfate) and the solvent removed in vacuo to give the title compound as a colourless oil (91.0 g).

$^1$H NMR (400 MHz, CDCl$_3$): δ –0.08 (s, 3H), 0.11 (s, 3H), 0.90 (s, 9H), 3.39-3.48), m, 2H), 3.91 (s, 3H), 4.82-4.85 (m, 1H), 5.19 (s, 2H), 7.01 (d, 1H), 7.30-7.51 (m, 6H), 7.81 (br s, 1H). LRMS: m/z ES$^+$ 501, 503 [M+Na]$^+$.

Preparation 2

[2-(Benzyloxy)-5-((1R)-2-bromo-1-{[tert-butyl(dimethyl)silyl]oxy}ethyl)phenyl]methanol Borane dimethylsulfide complex (42.4 ml of ~10M solution, 424 mmol) was added dropwise to a solution of preparation 1 (91.0 g, 189 mmol) in tetrahydrofuran (1600 ml). The resulting mixture was then heated to reflux for 2 hours and then cooled to 0° C. before quenching with methanol (270 ml). The mixture was left to stir at room temperature for 16 hours and then the solvent removed in vacuo. The residue was partitioned between dichloromethane (500 ml) and water (500 ml). The aqueous phase was separated and extracted with dichloromethane (500 ml) and the combined organic solutions washed with saturated aqueous sodium chloride (500 ml), dried over magnesium sulfate and the solvent removed in vacuo. The residue was purified by column chromatography on silica gel eluting with cyclohexane:ethyl acetate (100:0 changing to 80:20, by volume) to give the title compound (68.7 g) as a colourless oil.

$^1$H NMR (400 MHz, CDCl$_3$): δ –0.07 (s, 3H), 0.11 (s, 3H), 0.90 (s, 9H), 3.40-3.48 (m, 2H), 4.74 (s, 2H), 4.81-4.84 (m, 1H), 5.12 (s, 2H), 6.94 (d, 1H), 7.25-7.29 (m, 3H), 7.36-7.42 (m, 5H). LRMS: m/z ES$^+$ 473, 475 [M+Na]$^+$.

Preparation 3

(3-Bromo-phenyl)-acetic acid methyl ester

Acetyl chloride (0.7 ml, 9.3 mmol) was slowly added to a solution of (3-bromo-phenyl)-acetic acid (20.0 g, 93 mmol) in methanol (500 ml) at 0° C. under nitrogen and the reaction was allowed to warm gradually to room temperature over 5 hours. The solvent was removed under reduced pressure and the residue dissolved in dichloromethane, dried (sodium sulphate) and concentrated under reduced pressure to give the title compound as a colourless oil, 20.6 g.

$^1$H NMR (CDCl$_3$, 400 MHz), δ: 3.59 (s, 2H), 3.70 (s, 3H), 7.17-7.24 (m, 2H), 7.37-7.45 (m, 2H). LRMS: m/z ES$^+$ 253 [M+Na]$^+$.

Preparation 4

[3-(2-Oxo-propyl)-phenyl]-acetic acid methyl ester

A mixture of the bromide from preparation 3 (15.0 g, 65.0 mmol), tributyltin methoxide (28.3 ml, 98.0 mmol), isopropenyl acetate (10.8 ml, 98.0 mmol), palladium(II) acetate (750 mg, 3.30 mmol) and tri-ortho-tolylphosphine (2.0 g, 6.5 mmol) were stirred together in toluene (75 ml) at 100° C. under nitrogen for 5 hours. After cooling the reaction was diluted with ethyl acetate (150 ml) and 4M aqueous potassium fluoride solution (90 ml) and the mixture stirred for 15 minutes. The mixture was filtered through Arbocel®) and the organic phase separated and reduced under reduced pressure. The residue was purified by column chromatography on silica gel eluting with a solvent gradient of diethyl ether:pentane:dichloromethane (0:100:0 to 25:75:0 to 0:0:100, by volume) to give the title compound as a pale yellow oil, 12.6 g.

$^1$H nmr (CDCl$_3$, 400 MHz), δ: 2.15 (s, 3H), 3.61 (s, 2H), 3.69 (m, 5H), 7.10-7.13 (m, 2H), 7.19 (d, 1H), 7.30 (dd, 1H). LRMS: m/z ES$^+$ 224 [M+NH$_4$]$^+$.

Preparation 5

{3-[(2R)-2-((1R)-1-Phenyl-ethylamino)-propyl]-phenyl}-acetic acid methyl ester hydrochloride A solution of the ketone from preparation 4 (8.5 g, 41.2 mmol), (R)-α-methyl benzylamine (4.8 ml, 37.2 mmol), sodium triacetoxyborohydride (11.6 g, 56 mmol) and acetic acid (2.2 ml, 38 mmol) in dichloromethane (400 ml) was stirred at room temperature for 48 hours. The reaction mixture was quenched by addition of saturated aqueous sodium bicarbonate solution (200 ml) and allowed to stir until effervescence ceased. The organic phase was separated and the aqueous phase extracted with dichloromethane (100 ml). The combined organic solutions were dried (magnesium sulphate) and concentrated under reduced pressure. Purification by column chromatography on silica gel eluting with dichloromethane:methanol:88 ammonia (99:1:0.1 to 95:5:0.5 by volume) gave a 4:1 mixture of diastereomers (R,R major) as a pale yellow oil (8.71 g). Treatment with excess 1M hydrogen chloride in methanol followed by three successive crystallisations (diisopropylether/methanol) gave the title compound as a colourless crystalline solid, 5.68 g.

$^1$H nmr (CD$_3$OD, 400 MHz), δ: 1.18 (d, 3H), 1.68 (d, 3H), 2.60-2.66 (m, 1H), 3.15-3.26 (m, 1H), 3.25-3.30 (m, 1H), 3.30 (s, 3H), 3.62 (s, 2H), 4.59 (q, 1H), 7.00 (m, 2H), 7.17 (m, 1H), 7.27 (m, 1H), 7.50 (m, 5H). LRMS: m/z ES$^+$ 312 [M+H]$^+$.

Preparation 6

Methyl {3-[(2R)-2-aminopropyl]phenyl}acetate

A solution of the compound from preparation 5 (7.69 g, 22 mmol) and ammonium formate (6.94 g, 110 mmol) in ethanol (40 ml) was heated to 75° C. in the presence of 20% palladium hydroxide-on-charcoal (Pd(OH)$_2$/C, 2.00 g). After 90 minutes the reaction mixture was cooled to room temperature, filtered through Arbocel® and the filtrate concentrated in vacuo. The residue was partitioned between dichloromethane (100 ml) and 0.88 ammonia (100 ml) and the organic phase separated. The aqueous phase was extracted with dichloromethane (100 ml) and the combined organic extracts dried over magnesium sulfate and reduced in vacuo to give the title compound as a colourless oil (4.78 g).

$^1$H NMR (400 MHz, CD$_3$OD): δ 1.06 (d, 3H), 2.57-2.67 (m, 2H), 3.05-3.12 (m, 1H), 3.63 (s, 3H), 3.67 (s, 3H), 7.11 (m, 3H), 7.25 (m, 1H). LRMS: m/z ES$^+$ 208 [M+H]$^+$.

Preparation 7

Methyl (3-{(2R)-2-[(2R)-2-{[tert-butyl(dimethyl)silyl]oxy}-2-(4-[benzyloxy]-3-hydroxymethyl-phenyl)-ethylamino]-propyl}-phenyl)-acetate A solution of the bromide from preparation 2 (12.5 g, 27.7 mmol) and the amine from preparation 6 (11.5 g, 55.4 mmol) in dichloromethane (130 ml) was heated to 90° C., allowing the dichloromethane to evaporate. The resulting melt was left at 90° C. for a further 16 hours. The reaction mixture was cooled to room temperature and purified by column chromatography on silica gel eluting with dichloromethane:methanol:0.88 ammonia (98:2:0.2 to 97:3:0.3, by volume) to give the title compound (12.1 g) as a colourless oil.

$^1$H NMR (400 MHz, CD$_3$OD): δ −0.19 (s, 3H), 0.00 (s, 3H), 0.83 (s, 9H), 1.05 (d, 3H), 2.55-2.68 (m, 3H), 2.80-2.95 (m, 2H), 3.58 (s, 2H), 3.66 (s, 3H), 4.67 (d, 2H), 4.74 (t, 1H), 5.12 (s, 3H), 6.92 (d, 1H), 7.00 (d, 1H), 7.03 (s, 1H), 7.07-7.13 (m, 2H), 7.15-7.19 (m, 1H), 7.29-7.39 (m, 4H), 7.46 (m, 2H). LRMS: m/z ES$^+$ 578 [M+H]$^+$.

Preparation 8

Methyl (3-{(2R)-2-[(2R)-2-{[tert-butyl(dimethyl)silyl]oxy}-2-(4-hydroxy-3-hydroxymethyl-phenyl)-ethylamino]-propyl}-phenyl)-acetate A suspension of compound from preparation 7 (5.27 g, 9.12 mmol) and 10% palladium on carbon (1.00 g) in ethanol (50 ml) was stirred under an atmosphere of hydrogen (60 psi) at room temperature for 16 hours. The catalyst was filtered off through Arbocel® and the filtrate concentrated in vacuo. The residue was purified by column chromatography on silica gel eluting with dichloromethane:methanol:0.88 ammonia (96:4:0.4 to 95:5:0.5, by volume) to give the title compound as a pale yellow oil (1.99 g).

$^1$H NMR (400 MHz, CD$_3$OD): δ −0.20 (s, 3H), −0.01 (s, 3H), 0.82 (s, 9H), 1.06 (d, 3H), 2.55-2.69 (m, 3H), 2.86-2.96 (m, 2H), 3.59 (s, 2H), 3.67 (s, 3H), 4.62 (d, 2H), 4.70 (t, 1H), 6.68 (d, 1H), 6.98-7.03 (m, 3H), 7.10 (d, 1H), 7.19 (m, 2H). LRMS: m/z ES$^+$ 488 [M+H]$^+$.

Preparation 9

(3-{(2R)-2-[(2R)-2-{[tert-Butyl(dimethyl)silyl]oxy}-2-(4-hydroxy-3-hydroxymethyl-phenyl)-ethylamino]-propyl}-phenyl)-acetic acid A solution of the ester from preparation 8 (7.04 g, 14.43 mmol) in tetrahydrofuran (40 ml) was treated with lithium hydroxide (28.9 ml of a 1M aqueous solution, 28.9 mmol) and the reaction left to stir at room temperature for 16 hours. Hydrochloric acid (28.9 ml of a 1M aqueous solution, 28.9 mmol) was added and the tetrahydrofuran was removed in vacuo. The remaining aqueous layer was decanted and the residue washed with further water (10 ml). The residue was redissolved in methanol (30 ml) and the solvent removed in vacuo to give the title compound as a colorless foam (5.95 g).

$^1$H NMR (400 MHz, CD$_3$OD): −0.13 (s, 3H), 0.06 (s, 3H), 0.86 (s, 9H), 1.22 (d, 3H), 2.72-2.77 (dd, 1H), 2.93-2.98 (dd, 1H), 3.09-3.13 (dd, 1H), 3.23-3.28 (dd, 1H), 3.43-3.48 (m, 1H), 3.48 (s, 2H), 4.64 (d, 2H), 4.97 (m, 1H), 6.78 (d, 1H), 7.02 (d, 1H), 7.11 (d, 1H), 7.13 (s,1H), 7.18-7.25 (m, 2H), 7.32 (s, 1H). LRMS: ES$^+$ m/z 474 [M+H]$^+$ Microanalysis found: C 64.15, H 8.25, N 2.84; C$_{26}$H$_{39}$NO$_5$Si+0.7H$_2$O requires C 64.22, H 8.37, N 2.88%.

Preparation 10

Methyl 4-{[({3-[(2R)-2-({(2R)-2-{[tert-butyl(dimethyl)silyl]oxy}-2-[4-hydroxy-3-(hydroxymethyl)phenyl]ethyl}amino)propyl]phenyl}acetyl)amino]methyl}benzoate 1-(3-Dimethylaminopropyl)-3-ethylcarbodiimide hydrochloride (1.44 g, 9.28 mmol) was added to a mixture of the acid from preparation 9 (4.0 g, 8.22 mmol), methyl 4-(aminomethyl) benzoate (1.54 g, 9.28 mmol), 1-hydroxybenzotriazole hydrate (1.25 g, 9.28 mmol) and triethylamine (3.53 g, 25.3 mmol) in N,N-dimethylformamide (60 ml) and the reaction was stirred at room temperature for 64 hours. The mixture was concentrated under reduced pressure and the oily residue partitioned between dichloromethane (50 ml) and sodium bicarbonate solution (50 ml), and the layers separated. The aqueous solution was extracted with further dichloromethane (3×75 ml), the combined organic solutions were washed with water (30 ml) and brine (30 ml), dried over sodium sulphate and evaporated under reduced pressure. The residual orange oil was purified by column chromatography on silica gel using dichloromethane:methanol:0.88 ammonia (95:5:0.5) as eluant to afford the title compound as a white solid, 3.03 g.

$^1$H NMR (CD$_3$OD, 400 MHz), δ: −0.18 (s, 3H), 0.02 (s, 3H), 0.84 (s, 9H), 1.04 (d, 3H), 2.53 (m, 1H), 2.60-2.70 (m, 2H), 2.82-2.94 (m, 2H), 3.52 (s, 2H), 3.86 (s, 3H), 4.42 (s, 2H), 4.61 (d, 2H), 4.66 (m, 1H), 6.64-6.70 (d, 1H), 6.86-7.02 (br d, 2H), 7.04 (s, 1H), 7.17 (d, 1H), 7.20 (m, 2H), 7.24-7.36 (d, 2H), 7.86-7.92 (d, 2H). LRMS: m/z 621 [M+H]$^+$.

Preparation 11

4-{[({3-[(2R)-2-({(2R)-2-{[tert-Butyl(dimethyl)silyl]oxy}-2-[4-hydroxy-3-(hydroxymethyl)phenyl]ethyl}amino)propyl]phenyl}acetyl)amino]methyl}benzoic acid Aqueous lithium hydroxide solution (9.76 ml, 1M, 9.76 mmol) was added to a solution of the ester from preparation 10 (3.03 g, 4.88 mmol) in tetrahydrofuran (20 ml) and the reaction stirred at room temperature for 7 hours. The mixture was cooled in ice and neutralised by the addition of 1M hydrochloric acid (9.76 ml, 1M, 9.76 mmol). Tetrahydrofuran was removed in vacuo, and the remaining aqueous solution decanted off. The residue was azeotroped with methanol to afford the title compound as a white solid, 2.96 g.

$^1$H NMR (CD$_3$OD, 400 MHz), δ: −0.17 (s, 3H), 0.07 (s, 3H), 0.86 (s, 9H), 1.17 (d, 3H), 2.66-2.72 (dd, 1H), 2.98-3.03 (dd, 1H), 3.13 (dd, 1H), 3.24 (m, 1H), 3.40 (m, 1H), 3.55 (s, 2H), 4.40 (s, 2H), 4.67 (d, 2H), 4.97-5.00 (m, 1H), 6.79 (d, 1H), 7.09-7.15 (m, 3H), 7.20-7.36 (m, 5H), 7.87-7.89 (d, 2H). LRMS: m/z 607 [M+H]$^+$.

Preparation 12 tert-Butyl(4-{[(3,4-dimethoxybenzyl)amino]carbonyl}benzyl)carbamate

A mixture of 4-(tert-butoxycarbonylamino-methyl)-benzoic acid (1.0 g, 4 mmol), 1-(3-dimethylaminopropyl)-3-ethylcarbodiimide hydrochloride (920 mg, 4.8 mmol), 1-hydroxybenzotriazole hydrate (600 mg, 4.4 mmol), 3,4-dimethoxybenzylamine (730 mg, 4.4 mmol) and N-ethyldiisopropylamine (2.5 ml, 14 mmol) in N,N-dimethylformamide (20 ml) was stirred at room temperature for 18 hours. The mixture was concentrated under reduced pressure and the residue dissolved in ethyl acetate. This solution was washed with 1N hydrochloric acid (2×), sodium bicarbonate solution (2×) and sodium chloride solution. The solution was dried over magnesium sulphate and evaporated under reduced pressure to afford the title compound as a colourless solid, 1.6 g.

$^1$H NMR (CDCl$_3$, 400 MHz), δ: 1.44 (s, 9H), 3.84 (s, 6H), 4.35 (s, 2H), 4.58 (d, 2H), 4.98 (br s, 1H), 6.42 (s, 1H), 6.81 (d, 1H), 6.88 (m, 2H), 7.36 (d, 2H), 7.76 (d, 2H). LRMS: m/z APCl$^+$ 401 [M+H$^+$].

Preparation 13 tert-Butyl(4-{[(4-phenoxybenzoyl)amino]methyl}benzyl)carbamate 1-(3-Dimethylaminopropyl)-3-ethylcarbodiimide hydrochloride (722 mg, 4.65 mmol) was added to a solution of 1-hydroxybenzotriazole hydrate (628 mg, 4.65 mmol), 4-phenoxybenzoic acid (996 mg, 4.65 mmol), tert-butyl 4-aminomethylbenzyl carbamate (1.0 g, 4.23 mmol) and triethylamine (1.79 ml, 12.7 mmol) in N,N-dimethylformamide (50 ml) and the reaction stirred at room temperature for 18 hours. The mixture was concentrated under reduced pressure and the residue was partitioned between ethyl acetate (50 ml) and water (20 ml) and the layers separated. The aqueous solution was further extracted with ethyl acetate (5×50 ml) and the combined organic solutions were washed with water (20 ml), dried over sodium sulphate and evaporated under reduced pressure. The crude product was purified by column chromatography on silica gel using an elution gradient of dichloromethane:methanol (100:0 to 98:2) to afford the title compound as a white solid, 647 mg.

$^1$H NMR (CD$_3$OD, 400 MHz), δ: 1.44 (s, 9H), 4.19 (s, 2H), 4.54 (s, 2H), 7.00 (d, 2H), 7.05 (d, 2H), 7.16-7.24 (m, 3H), 7.30 (d, 2H), 7.40 (m, 2H), 7.84 (d, 2H). LRMS: m/z 455 [M+Na$^+$].

Preparation 14 tert-Butyl{4-[(1-naphthoylamino)methyl]benzyl}carbamate

The title compound was obtained as a pale brown solid in 79% yield from 1-naphthoic acid and tert-butyl 4-aminomethylbenzyl carbamate, following the procedure described in preparation 13.

$^1$H NMR (DMSO-d$_6$, 400 MHz), δ: 1.37 (s, 9H), 4.10 (d, 2H), 4.50 (d, 2H), 7.21 (d, 2H), 7.31-7.39 (m, 3H), 7.53 (m, 3H), 7.62 (d, 1H), 7.93-8.02 (m, 2H), 8.17 (m, 1H), 9.05 (m, 1H).

Preparation 15 tert-Butyl(4-{[(4-ethoxybenzoyl)amino]methyl}benzyl)carbamate

A solution of 4-ethoxybenzoyl chloride (702 mg, 3.80 mmol) in dichloromethane (5 ml) was added dropwise to an ice-cooled solution of tert-butyl 4-aminomethylbenzyl carbamate (1.0 g, 4.23 mmol) and triethylamine (1.60 ml, 11.4 mmol) in dichloromethane (45 ml). Once addition was complete, the reaction was allowed to warm to room temperature and stirred for 18 hours. The reaction was washed with sodium bicarbonate solution (25 ml), and the aqueous solution re-extracted with dichloromethane (4×50 ml). The combined organic solutions were washed with water (2×25 ml), dried over sodium sulphate and evaporated under reduced pressure. The crude product was purified by column chromatography on silica gel using dichloromethane:methanol (99:1) to give the title compound as a white solid, 656 mg.

$^1$H NMR (DMSO-d$_6$, 400 MHz), δ: 1.30-1.36 (m, 12H), 4.03-4.09 (m, 4H), 4.40 (d, 2H), 6.95 (d, 2H), 7.15 (d, 2H), 7.22 (d, 2H), 7.33 (m, 1H), 7.83 (d, 2H), 8.82 (m, 1H).

Preparation 16

N-[4-(Aminomethyl)benzyl]-4-ethoxybenzamide hydrochloride

A solution of the compound from preparation 15 (656 mg, 1.88 mmol) in 4M hydrochloric acid in dioxan (4.71 ml, 18.8 mmol) was stirred at room temperature for 1Hour. The reaction mixture was evaporated under reduced pressure to afford the title compound as a white solid.

$^1$H NMR (DMSO-d$_6$, 400 MHz), δ: 1.32 (t, 3H), 3.95 (m, 2H), 4.03-4.09 (q, 2H), 4.43 (d, 2H), 6.95 (d, 2H), 7.32 (d, 2H), 7.40 (d, 2H), 7.84 (d, 2H), 5.37 (m, 3H), 8.95 (m, 1H). LRMS: m/z APCl$^+$ 285 [M+H$^+$].

Preparations 17 to 18
The following compounds of general formula:

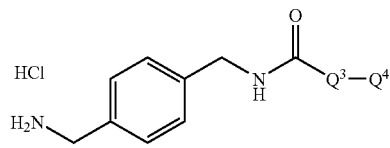

were prepared from the corresponding protected amines, following a similar procedure to that described in preparation 16.

$^1$H NMR (CD$_3$OD, 400 MHz), δ: 3.82 (s, 6H), 4.19 (s, 2H), 4.52 (s, 2H), 6.92 (s, 2H), 6.99 (s, 1H), 7.68 (d, 2H), 7.96 (d, 2H). LRMS: m/z APCl$^+$ 301 [M+H$^+$].

Preparation 20

Benzyl[4-(aminomethyl)benzyl]carbamate

A solution of benzylchloroformate (10.48 ml, 74 mmol) in dichloromethane (250 ml) was added to an ice-cooled solution of 4-aminomethyl benzylamine (10 g, 74 mmol) and triethylamine (9.77 ml, 74 mmol), in dichloromethane (480 ml) over 90 minutes. The mixture was concentrated under reduced pressure and the residue partitioned between ethyl acetate (450 ml) and 1M sodium hydroxide solution (300 ml). The resulting mixture was filtered, the layers separated and the organic phase dried over magnesium sulphate and evaporated under reduced pressure. The residue was dissolved in hot ethyl acetate, the solution cooled in an ice-bath, the resulting solid filtered off, and the filtrate evaporated under reduced pressure to afford the title compound as a white solid, 7.44 g.

$^1$H NMR (DMSO-d$_6$, 400 MHz), δ: 3.63 (s, 2H), 4.18 (s, 2H), 5.01 (s, 2H), 7.12-7.39 (m, 9H), 7.77 (s, 1H). LRMS: m/z ES$^+$ 271 [M+Na$^+$].

Preparation 21

Benzyl(4-{[(diphenylacetyl)amino]methyl}benzyl)carbamate 1-(3-Dimethylaminopropyl)-3-ethylcarbodiimide hydrochloride (0.39 g, 2.03 mmol) was added to a solution of 1-hydroxybenzotriazole hydrate (270 mg, 2.03 mmol), triethylamine (0.52 ml, 3.70 mmol), the amine from preparation 20 (500 mg, 1.85 mmol) and diphenylacetic acid (450 mg,

| Prep. No. | Q$^3$—Q$^4$ | Data |
|---|---|---|
| 17 | | $^1$H NMR(DMSO-d$_6$, 400 MHz) δ: 3.99(m, 2H), 4.52(d, 2H), 7.42(d, 2H), 7.46(d, 2H), 7.54(m, 3H), 7.63(d, 1H), 7.95-8.02(m, 2H), 8.17(dd, 1H), 8.37(br s, 2H), 9.13(m, 1H). LRMS: m/z ES$^-$ 289[M – H]$^-$ |
| 18 | | $^1$H NMR(DMSO-d$_6$, 400 MHz) δ: 3.97(s, 2H), 4.45(d, 2H), 7.03(m, 4H), 7.20(m, 1H), 7.33(d, 2H), 7.38-7.44(dd, 4H), 7.90(d, 2H), 8.12(br s, 2H), 9.03(m, 1H). LRMS: m/z ES$^-$ 331[M – H]$^-$ |

Preparation 19

4-(Aminomethyl)-N-(3,4-dimethoxybenzyl)benzamide hydrochloride

Hydrogen chloride was bubbled through an ice-cooled solution of the compound from preparation 12 (1.6 g, 4.0 mmol) in dichloromethane (30 ml) until saturation was achieved. The solution was then stirred at room temperature for 2 hours. The solution was evaporated under reduced pressure the residue triturated well with ether and the resulting solid filtered off and dried to afford the title compound, 1.04 g.

2.03 mmol) in dichloromethane (7 ml) and the reaction stirred at room temperature for 18 hours. The reaction mixture was partitioned between dichloromethane (10 ml) and water (10 ml) and the layers separated. The organic phase was dried over magnesium sulphate and concentrated under reduced pressure. The residue was triturated with hot dichloromethane, the solid filtered off and the filtrate evaporated under reduced pressure to give the title compound as a white solid, 291 mg.

$^1$H NMR (DMSO-d$_6$, 400 MHz), δ: 4.17 (d, 2H), 4.22 (s, 2H), 4.98 (s, 1H), 5.02 (s, 2H), 7.04-7.39 (m, 19H), 7.75 (m, 1H), 8.70 (m, 1H). LRMS: m/z ES$^-$ 463 [M–H].

Preparation 22

N-[4-(Aminomethyl)benzyl]-2,2-diphenylacetamide

A mixture of the compound from preparation 21 (200 mg, 0.43 mmol) and 10% palladium on charcoal (40 mg) in ethanol (15 ml) and ethyl acetate (few drops) was hydrogenated at 50° C. and 60 psi for 3 hours. The reaction mixture was filtered through Arbocel®, and the filtrate evaporated under reduced pressure. The crude product was purified by column chromatography on silica gel using dichloromethane:methanol (98:2 to 90:10) to afford the title compound as a white solid, 87 mg.

$^1$H NMR (DMSO-$d_6$, 400 MHz), δ: 3.63 (s, 2H), 4.24 (s, 2H), 5.00 (s, 2H), 7.08-7.37 (m, 14H), 8.70 (s, 1H).

Preparation 23

4-{[(Diphenylmethyl)amino]methyl}benzonitrile

A mixture of para-cyanobenzyl bromide (13.72 g, 70 mmol), benzhydrylamine (13.79 g, 70 mmol) and potassium carbonate (16.8 g, 70 mmol) in ethanol (200 ml) was stirred under reflux for 5 hours. The mixture was allowed to cool, the resulting precipitate filtered off and the filtrate evaporated under reduced pressure. The residue was recrystallised from 80-100 petrol/isopropanol to give the title compound as an oil, 14.5 g.

m.p. 75-75° C.

Preparation 24

[4-(Aminomethyl)benzyl](diphenylmethyl)amine dihydrochloride

A solution of the compound from preparation 23 (10.43 g, 35 mmol) in tetrahydrofuran (100 ml) was added dropwise over 20 minutes to a solution of lithium aluminium hydride (2.66 g, 70 mmol) in tetrahydrofuran (80 ml). Once addition was complete the reaction was stirred under reflux for 5 hours, then allowed to cool to room temperature. Water (2.7 ml), then 2M sodium hydroxide solution (2.7 ml) followed by further water (8.1 ml) were carefully added with stirring. The resulting mixture was filtered, the filtrate evaporated under reduced pressure, the residue dissolved in chloroform and the solution dried over sodium sulphate and evaporated under reduced pressure. The residue was treated with ethereal hydrochloric acid and the product recrystallised from isopropanol/methanol to afford the title compound, 3.6 g.

Microanalysis found: 67.50, H, 6.40; N, 7.55. $C_{21}H_{22}N_2$+2HCl requires C, 67.20; H, 6.45; N, 7.46%.

Preparation 25

N-Benzyl-3-cyanobenzenesulfonamide

Benzylamine (1.17 g, 10 mmol) was added to a solution of 3-cyanobenzene sulphonyl chloride (2 g, 10 mmol) and triethylamine (3.45 ml, 25 mmol) in tetrahydrofuran (30 ml) and the mixture stirred at room temperature for 18 hours. The mixture was diluted with water (30 ml), and extracted with ethyl acetate (50 ml). The organic extract was dried over sodium sulphate and evaporated under reduced pressure to give the title compound as a solid, 2.53 g.

$^1$H NMR (CD$_3$OD, 400 MHz), δ: 4.17 (s, 2H), 7.17 (m, 5H), 7.62 (dd, 1H), 7.88 (d, 1H), 8.02 (m, 2H). LRMS: m/z APCl$^+$ 271 [M+H$^+$].

Preparation 26

3-(Aminomethyl)-N-benzylbenzenesulfonamide hydrochloride

Sodium borohydride (3.23 g, 100 mmol) was added portionwise over 20 minutes to an ice-cooled solution of cobalt chloride (2.22 g, 17.2 mmol) and the nitrile from preparation 25 (2.33 g, 8.5 mmol) in methanol (120 ml), and once addition was complete, the reaction was stirred at room temperature for 4 hours. The reaction was quenched by the addition of hydrochloric acid (3N, 15 ml), then 0.88 ammonia (20 ml) was added. The mixture was concentrated under reduced pressure and the residue pre-adsorbed onto silica gel. This was purified by column chromatography on silica gel using dichloromethane:methanol:0.88 ammonia (97:3:0.5 to 90:10:1) to afford the an oil. The oil was treated with methanolic hydrochloric acid (1M), and the solution evaporated under reduced pressure to afford the title compound as a white solid, 2.42 g.

$^1$H NMR (CD$_3$OD, 400 MHz), δ: 4.09 (s, 2H), 4.19 (s, 2H), 7.20 (m, 5H), 7.61 (m, 1H), 7.68 (m, 1H), 7.86(m, 1 H), 7.94(s, 1 H). LRMS: m/z APCl$^+$ 277 [M+H$^+$].

Preparation 27 tert-Butyl(4-{[(1H-imidazol-1-ylcarbonyl)amino]methyl}benzyl)carbamate

A mixture of N,N-carbonyl diimidazole (1.51 g, 9.31 mmol) and tert-butyl 4-aminomethylbenzyl carbamate (2 g, 8.45 mmol) in tetrahydrofuran (60 ml) was stirred at room temperature for 18 hours. The reaction was concentrated under reduced pressure and the residue partitioned between ethyl acetate (30 ml) and water (30 ml) and the layers separated. The aqueous solution was further extracted with ethyl acetate (2×30 ml) and the combined organic solutions evaporated under reduced pressure. The crude product was purified by column chromatography on silica gel using dichloromethane:methanol:0.88 ammonia (95:5:0.5) as eluant to afford the title compound as a colourless oil.

$^1$H NMR (CD$_3$OD, 400 MHz), δ: 1.44 (s, 9H), 4.20 (s, 2H), 4.51 (s, 2H), 7.05 (s, 1H), 7.25 (d, 2H), 7.32 (d, 2H), 7.62 (s,1H), 8.26 (s, 1H). LRMS: m/z ES$^+$ 353 [M+Na$^+$].

Preparation 28 tert-Butyl{4-[({[(3-phenoxybenzyl)amino]carbonyl}amino)methyl]benzyl}carbamate

A mixture of the compound from preparation 27 (500 mg, 1.51 mmol), 3-phenoxybenzylamine (EP 0313397, pg 16) (345 mg, 1.59 mmol) and triethylamine (0.64 ml, 4.53 mmol) in toluene (20 ml) was stirred at 60° C. for 18 hours. The cooled mixture was concentrated under reduced pressure and the resulting residue was purified by column chromatography on Isolute® SCI gel using methanol as eluant to afford the title compound as a white solid, 342 mg.

$^1$H NMR (DMSO-$d_6$, 400 MHz), δ: 1.38 (s, 9H), 4.17 (s, 2H), 4.20 (s, 4H), 6.82 (dd, 1H), 6.90 (s, 1H), 7.00 (m, 2H), 7.14 (m, 4H), 7.22-7.40 (m, 6H). LRMS: ES$^-$ 460 [M−H]$^-$.

Preparation 29

N-[4-(Aminomethyl)benzyl]-N'-(3-phenoxybenzyl)urea hydrochloride

A solution of the compound from preparation 28 (451 mg, 0.98 mmol) in 4M hydrochloric acid in dioxan (2.44 ml, 9.77 mmol) was stirred at room temperature for 4 hours. The reaction mixture was evaporated under reduced pressure to give the title compound as a white solid.

$^1$H NMR (CD$_3$OD, 400 MHz), δ: 4.07 (s, 2H), 4.29 (d, 2H), 4.35 (s, 2H), 6.93 (m, 3H), 7.08 (dd, 1H), 7.26 (d, 2H), 7.31 (d, 1H), 7.34-7.42 (m, 6H). LRMS: m/z 362 [M+H]$^+$.

Preparations 30 to 34

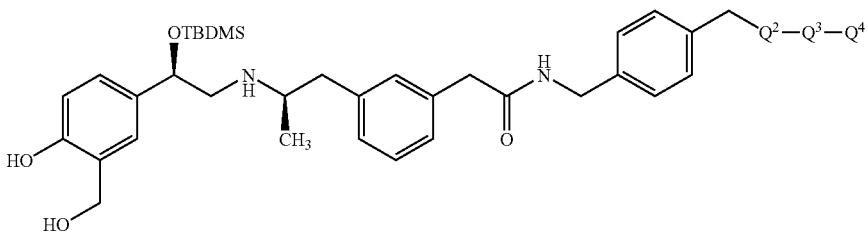

1-(3-Dimethylaminopropyl)-3-ethylcarbodiimide hydrochloride (1.1-1.3 eq) was added to a solution of 1-hydroxybenzotriazole hydrate (1.1-1.3 eq), the acid from preparation 9 (1 eq), the appropriate amine or amine salt (1.1-1.2 eq) and triethylamine (2-3 eq) in N,N-dimethylformamide (8-40 mlmmol$^{-1}$), and the reaction stirred at room temperature for 18 hours. The mixture was concentrated under reduced pressure and the residue partitioned between dichloromethane and saturated sodium bicarbonate solution. The layers were separated, the aqueous extracted with further dichloromethane and the combined organic solutions were dried over sodium sulphate and evaporated under reduced pressure. The crude product was purified by column chromatography on silica gel using dichloromethane:methanol:0.88 ammonia (95:5:0.5) as eluant to provide the title compounds.

| Prep. No. | $Q^2$—$Q^3$—$Q^4$ | Data |
|---|---|---|
| 30 | (N-CH(phenyl)$_2$) | $^1$H NMR(CD$_3$OD, 400 MHz) δ: −0.24(s, 3H), −0.05(s, 3H), 0.78(s, 9H), 0.98(d, 3H), 2.48(dd, 1H), 2.55-2.64(m, 2H), 2.79-2.86 (m, 2H), 3.45(s, 2H), 3.61(s, 2H), 4.30(s, 2H), 4.57(d, 2H), 4.64(m, 1H), 4.73(s, 1H), 6.93(d, 2H), 7.01(s, 1H), 7.08-7.18 (m, 9H), 7.23(m, 4H), 7.31(m, 4H). LRMS: m/z ES$^+$ 758[M + H$^+$] |
| 31 | (N-C(O)-C$_6$H$_4$-OCH$_2$CH$_3$) | $^1$H NMR(CD$_3$OD, 400 MHz) δ: −0.20(s, 3H), −0.01(s, 3H), 0.82(s, 9H), 1.03(d, 3H), 1.40(t, 3H), 2.54(dd, 1H), 2.60-2.70(m, 2H), 2.85-2.94 (m, 2H), 3.48(s, 2H), 4.07(q, 2H), 4.33(s, 2H), 4.51(d, 2H), 4.60(d, 2H), 4.69(m, 1H), 6.68(d, 1H), 6.95(m, 4H), 7.04(s, 1H), 7.12(d, 1H), 7.17(m, 4H), 7.26(d, 2H), 7.79(d, 2H). LRMS: m/z ES$^+$ 740[M + H$^+$] |
| 32 | (N-C(O)-CH(phenyl)$_2$) | $^1$H NMR(CD$_3$OD, 400 MHz) δ: −0.19(s, 3H), 0.00(s, 3H), 0.83(s, 9H), 1.03(d, 3H), 2.57(m, 1H), 2.65(m, 2H), 2.90(m, 2H), 3.48(s, 2H), 4.32(s, 2H), 4.36(s, 2H), 4.62(d, 2H), 4.69(m, 1H), 4.98(s, 1H), 6.67(d, 1H), 6.98(d, 2H), 7.04(s, 1H), 7.13-7.28(m, 17H). LRMS: m/z ES$^+$ 786[M + H$^+$] |
| 33 | (N-C(O)-naphthyl) | $^1$H NMR(CD$_3$OD, 400 MHz) δ: −0.20(s, 3H), −0.01(s, 3H), 0.82(s, 9H), 1.02(d, 3H), 2.53(dd, 1H), 2.65(m, 2H), 2.84-2.92(m, 2H), 3.49(s, 2H), 4.36(s, 2H), 4.60(s, 4H), 4.69(m, 1H), 6.68(d, 1H), 6.98(d, 2H), 7.05(s, 1H), 7.13(d, 1H), 7.18(m, 2H), 7.24(d, 2H), 7.37(d, 2H), 7.47-7.54(m, 3H), 7.59(d, 1H), 7.90(m, 1H), 7.96(d, 1H), 8.15(m, 1H). LRMS: m/z ES$^+$ 747[M + H$^+$] |

| Prep. No. | Q²—Q³—Q⁴ | Data |
|---|---|---|
| 34 | 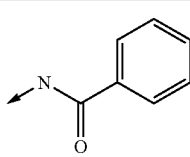 | ¹H NMR(CD₃OD, 400 MHz) δ: −0.23(s, 3H), −0.04(s, 3H), 0.78(s, 9H), 1.00(d, 3H), 2.47-2.53 (m, 1H), 2.58-2.66(m, 2H), 2.82-2.90(m, 2H), 3.44(s, 2H), 4.29(s, 2H), 4.49(s, 2H), 4.56(d, 2H), 4.67(m, 1H), 6.64(d, 1H), 6.93-6.96 (m, 4H), 7.01(m, 3H), 7.08(d, 1H), 7.12-7.18 (m, 5H), 7.23(d, 2H), 7.34-7.38(m, 2H), 7.79(d, 2H). LRMS: m/z ES⁻ 787[M − H⁻] |

Preparation 35

4-{[({3-[(2R)-2-({(2R)-2-{[tert-Butyl(dimethyl) silyl]oxy}-2-[4-hydroxy-3-(hydroxymethyl)phenyl] ethyl}amino)propyl]phenyl}acetyl)amino]methyl}-N-(3,4-dimethoxybenzyl)benzamide The title compound was obtained as a white foam in 71% yield, from the compounds of preparations 9 and 19, following the procedure described for preparations 30 to 34.
¹H NMR (CD₃OD, 400 MHz), δ: −0.19 (s, 3H), −0.01 (s, 3H), 0.83 (s, 9H), 1.03 (d, 3H), 2.56 (dd, 1H), 2.64 (m, 2H), 2.90 (m, 2H), 3.54 (s, 2H), 3.80 (s, 6H), 4.40 (s, 2H), 4.50 (s, 4H), 4.62 (m, 1H), 4.70 (m, 1H), 6.68 (d, 1H), 6.90 (s, 2H), 6.99 (d, 2H), 7.05 (s, 1H), 7.12-7.21 (m, 3H), 7.31 (d, 2H), 7.77 (d, 2H). LRMS: m/z APCl⁺ 756 [M⁺].

Preparation 36

N-{3-[(Benzylamino)sulfonyl]benzyl}-2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}acetamide The title compound was obtained as a white solid in 53% yield from the compounds from preparations 9 and 26, following the procedure described for preparations 30 to 34.

¹H NMR (CD₃OD, 400 MHz), δ: −0.19 (s, 3H), 0.00 (s, 3H), 0.83 (s, 9H), 1.04 (d, 3H), 2.53 (dd, 1H), 2.70 (m, 2H), 2.85-2.98 (m, 2H), 3.52 (s, 2H), 3.97 (s, 2H), 4.40 (s, 2H), 4.61 (q, 2H), 4.72 (m, 1H), 6.69 (d, 1H), 6.99 (m, 2H), 7.05 (s, 1H), 7.13-7.23 (m, 8H), 7.44 (m, 2H), 7.69 (m, 2H). LRMS: m/z ES⁺ 732 [M⁺].

Preparations 37 to 54

1-(3-Dimethylaminopropyl)-3-ethylcarbodiimide hydrochloride (1.1eq) was added to a solution of 1-hydroxybenzotriazole hydrate (1.1 eq), amine (RNH₂ 1 eq), the acid from preparation 11 (1 eq) and triethylamine (3 eq) in N,N-dimethylformamide (12-40 mlmmol⁻¹) and the reaction stirred at room temperature for 18 hours. The reaction mixture was concentrated under reduced pressure and the residue was partitioned between dichloromethane and water and the layers separated. The aqueous solution was further extracted with dichloromethane and the combined organic solutions were dried over sodium sulphate and evaporated under reduced pressure. The crude product was purified by column chromatography on silica gel using an elution gradient of dichloromethane:methanol:0.88 ammonia (100:0:0 to 95:5: 0.5) to afford the title compounds.

| Prep. No. | Q³—Q⁴ | Data |
|---|---|---|
| 37 | 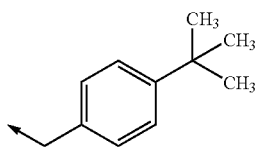 | ¹H NMR(CD₃OD, 400 MHz) δ: −0.20(s, 3H), −0.01(s, 3H), 0.82(s, 9H), 1.03(d, 3H), 1.29(s, 9H), 2.50-2.58(m, 1H), 2.59-2.70(m, 2H), 2.85-2.94(m, 2H), 3.51(s, 2H), 4.40(s, 2H), 4.51(s, 2H), 4.61(d, 2H), 4.64-4.71(m, 1H), 6.67(d, 1H), 6.98(m, 2H), 7.05(s, 1H), 7.13(d, 2H), 7.19(m, 2H), 7.25(d, 2H), 7.30(d, 2H), 7.35(d, 2H), 7.77(d, 2H). LRMS: m/z 752[M + H⁺] |
| 38 | 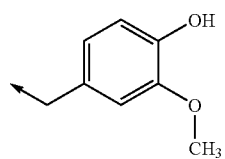 | ¹H NMR(CD₃OD, 400 MHz) δ: −0.17(s, 3H), 0.02(s, 3H), 0.84(s, 9H), 1.06(d, 3H), 2.55-2.60 (m, 1H), 2.67-2.73(m, 2H), 2.90-2.99(m, 2H), 3.52(s, 2H), 3.83(s, 3H), 4.41(s, 2H), 4.46(s, 2H), 4.62(m, 2H), 4.72(m, 1H), 6.68-6.82 (m, 3H), 6.93(d, 1H), 7.00(d, 2H), 7.06(s, 1H), 7.14(d, 1H), 7.20(m, 2H), 7.30(d, 2H), 7.76(d, 2H). LRMS: m/z 742[M + H⁺] |

| Prep. No. | Q³—Q⁴ | Data |
|---|---|---|
| 39 | H₃C–CH₂–O–(2-substituted phenyl)–CH₂– | ¹H NMR(CD₃OD, 400 MHz) δ: −0.20(s, 3H), −0.01(s, 3H), 0.82(s, 9H), 1.02(d, 3H), 1.41(t, 3H), 2.53(m, 1H), 2.60-2.68(m, 2H), 2.84-2.91 (m, 2H), 3.51(s, 2H), 4.06-4.12(q, 2H), 4.40(s, 2H), 4.57(s, 2H), 4.61(d, 2H), 4.64-4.69 (m, 1H), 6.67(d, 1H), 6.88(m, 1H), 6.93(d, 1H), 6.98(d, 2H), 7.05(s, 1H), 7.12-7.25 (m, 5H), 7.31(d, 2H), 7.77(d, 2H). LRMS: m/z 740[M + H⁺] |
| 40 | 4-(OCF₃)-phenyl-CH₂– | ¹H NMR(CD₃OD, 400 MHz) δ: −0.20(s, 3H), −0.01(s, 3H), 0.82(s, 9H), 1.03(d, 3H), 2.52-2.57 (m, 1H), 2.61-2.69(m, 2H), 2.82-2.92(m, 2H), 3.51(s, 2H), 4.40(s, 2H), 4.56(s, 2H), 4.61(d, 2H), 4.66-4.72(m, 1H), 6.67(d, 1H), 6.97(m, 2H), 7.05(s, 1H), 7.12-7.17(m, 1H), 7.18-7.23(m, 4H), 7.31(d, 2H), 7.42(m, 2H), 7.78(d, 2H). LRMS: m/z 780[M + H⁺] |
| 41 | 3,4-dichlorophenyl-CH₂– | ¹H NMR(CD₃OD, 400 MHz) δ: −0.20(s, 3H), −0.01(s, 3H), 0.82(s, 9H), 1.03(d, 3H), 2.48-2.57 (m, 1H), 2.60-2.70(m, 2H), 2.81-2.96(m, 2.57(m, 1H), 2.60-2.70(m, 2H), 2.81-2.96(m, 2H), 3.51(s, 2H), 4.41(s, 2H), 4.51(s, 2H), 4.61(d, 2H), 4.66-4.72(m, 1H), 6.67(d, 1H), 6.95-7.03(m, 2H), 7.03-7.08(m, 1H), 7.13(m, 1H), 7.16(m, 2H), 7.27(d, 1H), 7.32(d, 2H), 7.44-7.51(d, 2H), 7.78(d, 2H). LRMS: m/z 764[M + H⁺] |
| 42 | 4-F-3-(CF₃)-phenyl-CH₂– | ¹H NMR(CD₃OD, 400 MHz) δ: −0.20(s, 3H), −0.01(s, 3H), 0.82(s, 9H), 1.03(d, 3H), 2.56(m, 1H), 2.60-2.70(m, 2H), 2.85-2.92(m, 2H), 3.51(s, 2H), 4.41(s, 2H), 4.61(d, 2H), 4.64(s, 2H), 4.69(m, 1H), 6.67(d, 1H), 6.97(d, 2H), 7.05(s, 1H), 7.13(m, 1H), 7.19(m, 2H), 7.20-7.33(m, 3H), 7.60-7.65(m, 1H), 7.69(d, 1H), 7.78(d, 2H). LRMS: m/z 782[M + H⁺] |
| 43 | 3,5-bis(CF₃)-phenyl-CH₂– | ¹H NMR(CD₃OD, 400 MHz) δ: −0.20(s, 3H), −0.01(s, 3H), 0.82(s, 9H), 1.03(d, 3H), 2.51-2.57 (m, 1H), 2.61-2.67(m, 2H), 2.84-2.91(m, 2H), 3.51(s, 2H), 4.41(s, 2H), 4.61(d, 2H), 4.66-4.72(m, 3H), 6.67(d, 1H), 6.97(m, 2H), 7.05(s, 1H), 7.13(d, 1H), 7.19(m, 2H), 7.33(d, 2H), 7.79(d, 2H), 7.85(s, 1H), 7.93(s, 2H). LRMS: m/z 832[M + H⁺] |
| 44 | 3-phenyl-phenyl-CH₂– (biphenyl-3-ylmethyl) | ¹H NMR(CD₃OD, 400 MHz) δ: −0.24(s, 3H), −0.06(s, 3H), 0.78(s, 6H), 0.98(d, 3H), 2.42-2.49 (m, 1H), 2.55-2.60(m, 2H), 2.70-2.84(m, 2H), 3.46(s, 2H), 4.36(s, 2H), 4.57(m, 4H), 4.63(m, 1H), 6.63(d, 1H), 6.93(d, 2H), 7.00(s, 1H), 7.08(d, 1H), 7.13(m, 2H), 7.26-7.30 (m, 5H), 7.33-7.40(m, 4H), 7.44-7.49(m, 1H), 7.53-7.59(m, 4H), 7.75(d, 2H). LRMS m/z 772[M + H]⁺ |
| 45 | 4-(phenoxy)phenyl-CH₂– | ¹H NMR(CD₃OD, 400 MHz) δ: −0.20(s, 3H), −0.01(s, 3H), 0.82(s, 9H), 1.03(d, 3H), 2.49-2.56 (m, 1H), 2.59-2.68(m, 2H), 2.84-2.91(m, 2H), 3.51(s, 2H), 4.40(s, 2H), 4.52(s, 2H), 4.60(d, 2H), 4.64-4.70(m, 1H), 6.67(d, 1H), 6.92-6.99(m, 5H), 7.05(s, 2H), 7.07-7.14(m, 3H), 7.18(m, 2H), 7.29-7.36(m, 5H), 7.77(d, 2H). LRMS: m/z 788[M + H⁺] |

| Prep. No. | Q³—Q⁴ | Data |
|---|---|---|
| 46 | 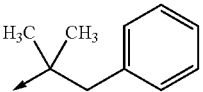 | ¹H NMR(CD₃OD, 400 MHz) δ: −0.19(s, 3H), −0.01(s, 3H), 0.83(s, 9H), 1.03(d, 3H), 1.40(s, 6H), 2.51-2.58(m, 1H), 2.60-2.71(m, 2H), 2.78-2.92(m, 2H), 3.16(s, 2H), 3.50(s, 2H), 4.39(s, 2H), 4.61(s, 2H), 4.65-4.73(m, 1H), 6.67(d, 1H), 6.97-7.02(m, 2H), 7.03-7.09 (m, 1H), 7.11-7.23(m, 8H), 7.23-7.30(br d, 2H), 7.57-7.64(br d, 2H).<br>LRMS: m/z 738[M + H⁺] |
| 47 | 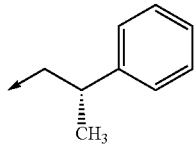 | ¹H NMR(CD₃OD, 400 MHz) δ: −0.20(s, 3H), −0.01(s, 3H), 0.82(s, 9H), 1.03(d, 3H), 1.29(d, 3H), 2.51-2.56(m, 1H), 2.60-2.69(m, 2H), 2.84-2.93(m, 2H), 3.06-3.16(m, 1H), 3.43-3.54(m, 4H), 4.38(s, 2H), 4.57-4.64(q, 2H), 4.67-4.72(m, 1H), 6.68(m, 1H), 6.98(d, 2H), 7.05(s, 1H), 7.12(d, 1H), 7.15-7.21(m, 3H), 7.22-7.33(m, 6H), 7.62(d, 2H).<br>LRMS: m/z 724[M + H⁺] |
| 48 | 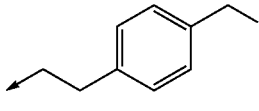 | ¹H NMR(CD₃OD, 400 MHz) δ: −0.19(s, 3H), −0.01(s, 3H), 0.82(s, 9H), 1.03(d, 3H), 1.19(t, 3H), 2.52-2.70(m, 5H), 2.83-2.92(m, 4H), 3.51-3.58(m, 4H), 4.39(s, 2H), 4.60(d, 2H), 4.66-4.72(m, 1H), 6.68(d, 1H), 6.98(m, 2H), 7.05(s, 1H), 7.09-7.15(m, 5H), 7.19(m, 2H), 7.28(d, 2H), 7.69(d, 2H).<br>LRMS: m/z 738[M + H⁺] |
| 49 | 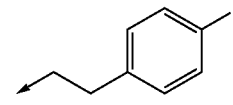 | ¹H NMR(CD₃OD, 400 MHz) δ: −0.19(s, 3H), −0.01(s, 3H), 0.82(s, 9H), 1.03(d, 3H), 2.52-2.70 (m, 3H), 2.83-2.92(m, 4H), 3.51-3.58(m, 4H), 4.39(s, 2H), 4.60(d, 2H), 4.66-4.72(m, 1H), 6.68(d, 1H), 6.98(m, 2H), 7.05(s, 1H), 7.16-7.34(m, 8H), 7.69(d, 2H).<br>LRMS: m/z 744[M + H⁺] |
| 50 | 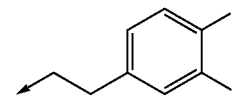 | ¹H NMR(CD₃OD, 400 MHz) δ: −0.19(s, 3H), −0.01(s, 3H), 0.82(s, 9H), 1.03(d, 3H), 2.52-2.58 (m, 1H), 2.60-2.71(m, 2H), 2.77(m, 2H), 2.88(m, 2H), 3.52(s, 2H), 3.58(t, 2H), 4.39(s, 2H), 4.60(d, 2H), 4.70(m, 1H), 6.68(d, 1H), 6.98(m, 2H), 7.05(s, 1H), 7.09-7.20(m, 4H), 7.29(d, 2H), 7.40(m, 2H), 7.69(d, 2H).<br>LRMS: m/z 778[M + H⁺] |
| 51 | 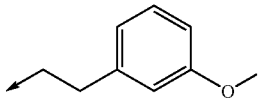 | ¹H NMR(CD₃OD, 400 MHz) δ: −0.23(s, 3H), −0.05(s, 3H), 0.79(s, 9H), 0.99(d, 3H), 2.49(dd, 1H), 2.57-2.65(m, 2H), 2.80-2.87 (m, 4H), 3.46(s, 2H), 3.52(t, 2H), 3.69(s, 3H), 4.35(s, 2H), 4.57(d, 2H), 4.65(dd, 1H), 6.64(d, 1H), 6.70(m, 1H), 6.76(m, 1H), 6.95(m, 2H), 7.01(s, 1H), 7.08-7.16(m, 4H), 7.24(d, 2H), 7.65(d, 2H).<br>LRMS: m/z 740[M + H⁺] |
| 52 | 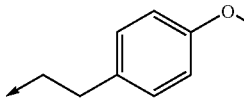 | ¹H NMR(CD₃OD, 400 MHz) δ: −0.20(s, 3H), −0.01(s, 3H), 0.82(s, 9H), 1.03(d, 3H), 1.35(t, 3H), 2.52-2.58(m, 1H), 2.60-2.70(m, 2H), 2.82(m, 2H), 2.85-2.93(m, 2H), 3.53(m, 4H), 3.98(q, 2H), 4.39(s, 2H), 4.60(d, 2H), 4.69(m, 1H), 6.68(d, 1H), 6.81(d, 2H), 6.99(m, 2H), 7.05(s, 1H), 7.13(m, 3H), 7.19(m, 2H), 7.28(d, 2H), 7.69(d, 2H).<br>LRMS: m/z 754[M + H⁺] |
| 53 | 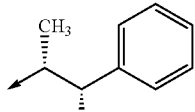 | ¹H NMR(CD₃OD, 400 MHz) δ: −0.20(s, 3H), 0.00(s, 3H), 0.82(s, 9H), 1.03(d, 3H), 1.20(d, 3H), 2.50-2.58(m, 1H), 2.61-2.72(m, 2H), 2.84-2.95(m, 2H), 3.53(s, 2H), 4.36(m, 1H), 4.39(s, 2H), 4.60(d, 2H), 4.69(m, 1H), 4.79(d, 1H), 6.68(d, 1H), 6.99(m, 2H), 7.05(s, 1H), 7.12-7.35(m, 8H), 7.41(d, 2H), 7.63(d, 2H).<br>LRMS: m/z ES⁺ 762[M + Na]⁺ |

| Prep. No. | Q³—Q⁴ | Data |
|---|---|---|
| 54 | | $^1$H NMR(CD$_3$OD, 400 MHz) δ: −0.20(s, 3H), −0.01(s, 3H), 0.82(s, 9H), 1.03(d, 3H), 2.52(m, 1H), 2.60-2.68(m, 2H), 2.82(t, 2H), 2.97(m, 2H), 3.50(s, 2H), 3.58-3.63(t, 2H), 4.39(s, 2H), 4.60(d, 2H), 4.67(m, 1H), 6.67(d, 1H), 6.97(m, 2H), 7.05(s, 1H), 7.12(d, 1H), 7.17(m, 1H), 7.27-7.33(m, 5H), 7.40(m, 2H), 7.52-7.59(m, 5H), 7.70(d, 2H). LRMS: m/z 786[M + H$^+$] |

Preparation 55

2-{3-[(2R)-2-({(2R)-2-{[tert-Butyl(dimethyl)silyl]oxy}-2-[4-hydroxy-3-(hydroxymethyl)phenyl]ethyl}amino)propyl]phenyl}-N-{4-[({[(3-phenoxybenzyl)amino]carbonyl}amino)methyl]benzyl}acetamide The title compound was obtained as a clear gum in 41% yield from the acid from preparation 11 and the amine from preparation 29, following the procedure described for preparations 37 to 54.

$^1$H NMR (CD$_3$OD, 400 MHz), δ: −0.20 (s, 3H), 0.01 (s, 3H), 0.82 (s, 9H), 1.03 (d, 3H), 2.49-2.58 (m, 1H), 2.60-2.72 (m, 2H), 2.82-2.94 (m, 2H), 3.50 (s, 2H), 3.80 (s, 2H), 4.34 (s, 4H), 4.60 (d, 2H), 4.67 (m, 1H), 6.67 (d, 1H), 6.90-7.36 (m, 19H). LRMS: m/z ES$^+$ 839 [M+Na$^+$].

In Vitro Activity of the Compounds of Formula (1)

The ability of the compounds of the formula (1) to act as potent β2 agonists therefore mediating smooth muscle relaxation may be determined by the measure of the effect of beta-2 adrenergic receptor stimulation on electrical field stimulated-contraction of guinea pig trachea strips.

Guinea-Pig Trachea

Male, Dunkin-Hartley guinea pigs (475-525 g) are killed by CO$_2$ asphyxiation and exsanguination from the femoral artery and the trachea is isolated. Four preparations are obtained from each animal, starting the dissection immediately below the larynx and taking 2.5 cm length of trachea. The piece of trachea is opened by cutting the cartilage opposite the trachealis muscle, then transverse sections, 3-4 cartilage rings wide, are cut. The resulting strip preparations are suspended in 5 ml organ baths using cotton threads tied through the upper and lower cartilage bands. The strips are equilibrated, un-tensioned, for 20 minutes in a modified Krebs Ringer buffer (Sigma K0507) containing 3 μM Indomethacin (Sigma I7378), 10 μM Guanethidine (Sigma G8520) and 10 μM Atenolol (Sigma A7655), heated at 37° C. and gassed with 95% O$_2$/5% CO$_2$, before applying an initial tension of 1 g. The preparations are allowed to equilibrate for a further 30-45 minutes, during which time they are re-tensioned (to 1 g) twice at 15-minute intervals. Changes in tension are recorded and monitored via standard isometric transducers coupled to a data-collection system (custom-designed at Pfizer). Following the tensioning equilibration, the tissues are subjected to electrical field stimulation (EFS) using the following parameters: 10 s trains every 2 minutes, 0.1 ms pulse width, 10 Hz and just-maximal voltage (25 Volts) continuously throughout the length of the experiment. EFS of post-ganglionic cholinergic nerves in the trachea results in monophasic contractions of the smooth muscle and twitch height is recorded. The organ baths are constantly perfused with the above-described Krebs Ringer buffer by means of a peristaltic pump system (pump flow rate 7.5 ml/minute) throughout the experiment, with the exception of when a beta-2 agonist according to the present invention is added, the pump is then stopped for the time of the cumulative dosing to the bath and started again after maximal response is reached for the wash-out period.

Experimental Protocol for Assessment of Potency and Efficacy

Following equilibration to EFS, the peristaltic pump is stopped and the preparations 'primed' with a single dose of 300 nM isoprenaline (Sigma I5627) to establish a maximal response in terms of inhibition of the contractile EFS response. The isoprenaline is then washed out over a period of 40 minutes. Following the priming and wash-out recovery, a standard curve to isoprenaline is carried out on all tissues (Isoprenaline Curve 1) by means of cumulative, bolus addition to the bath using half log increments in concentration. The concentration range used is $1^{e-9}$ to $1^e/3^{e-6}$ M. At the end of the isoprenaline curve the preparations are washed again for 40 minutes before commencing a second curve, either to isoprenaline (as internal control) or a beta-2 agonist according to the present invention. Beta-2 agonist responses are expressed as percentage inhibition of the EFS response. Data for beta-2 agonist are normalised by expressing inhibition as a percentage of the maximal inhibition induced by isoprenaline in Curve 1. The $EC_{50}$ value for beta-2 agonist according to the present invention refers to the concentration of compound required to produce half maximal effect. Data for beta-2 agonists according to the present invention are then expressed as relative potency to isoprenaline defined by the ratio ($EC_{50}$ beta-2 agonist)/(EC50 Isoprenaline).

Confirmation of Beta-2 Mediated Functional Activity

Beta-2 agonist activity of test compounds is confirmed using the protocol above, however, prior to constructing the curve to beta-2 agonist according to the present invention, the preparations are pre-incubated (for a minimum of 45 minutes) with 300 nM ICI 118551 (a selective β$_2$ antagonist) which results in the case of a beta-2 mediated effect in a rightward-shift of the test compound dose response curve.

According to another alternative, the agonist potency for the β2 receptor of the compounds of the formula (1) may also be determined by the measure of the concentration of compound according to the present invention required to produce half maximal effect ($EC_{50}$) for the β2 receptor.

Compound Preparation 10 mM/100% DMSO (dimethylsulfoxide) stock of compound is diluted to required top dose in 4% DMSO. This top dose is used to construct a 10-point semi-log dilution curve, all in 4% DMSO. Isoprenaline (Sigma, I-5627) was used as a standard in every experiment and for control wells on each plate. Data was expressed as % Isoprenaline response.

Cell Culture

CHO (Chinese Hamster Ovary) cells recombinantly expressing the human β2 adrenergic receptor (from Kobilka et al., PNAS 84: 46-50, 1987 and Bouvier et al., Mol Pharmacol 33: 133-139 1988 CHOhβ2) were grown in Dulbeccos MEM/NUT MIX F12 (Gibco, 21331-020) supplemented with 10% foetal bovine serum (Sigma, F4135, Lot 90K8404 Exp 09/04), 2 mM glutamine (Sigma, G7513), 500 µg/ml geneticin (Sigma, G7034) and 10 µg/ml puromycin (Sigma, P8833). Cells were seeded to give about 90% confluency for testing.

Assay Method

25 µl/well each dose of compound was transferred into a cAMP-Flashplate® (NEN, SMP004B), with 1% DMSO as basal controls and 100 nM Isoprenaline as max controls. This was diluted 1:2 by the addition of 25 µl/well PBS. Cells were trypsinised (0.25% Sigma, T4049), washed with PBS (Gibco, 14040-174) and resuspended in stimulation buffer (NEN, SMP004B) to give $1 \times 10^6$ cells/ml CHOhB2. Compounds were incubated with 50 µl/well cells for 1 Hour. Cells were then lysed by the addition of 100 µl/well detection buffer (NEN, SMP004B) containing 0.18 µCi/ml $^{125}$I-cAMP (NEN, NEX-130) and plates were incubated at room temperature for a further 2 hours. The amount of $^{125}$I-cAMP bound to the Flashplate® was quantified using a Topcount NXT (Packard), normal counting efficiency for 1 minute. Dose-response data was expressed as % Isoprenaline activity and fitted using a four parameter sigmoid fit.

It has thus been found that the compounds of formula (1) according to the present invention that are illustrated in examples 1 to 26 above show a β2 cAMP $EC_{50}$ below 1 nM.

The invention claimed is:

1. A compound of formula (1):

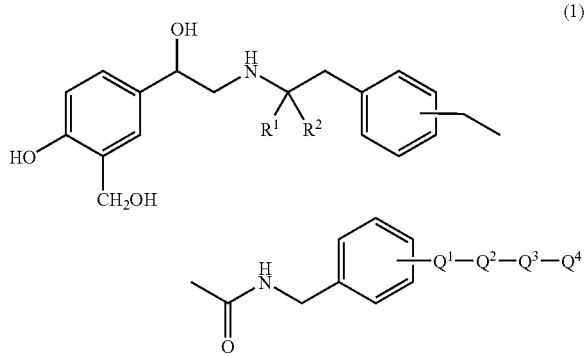

(1)

wherein the $CH_2$—$C(=O)NH$-benzyl-$Q^1$-$Q^2$-$Q^3$-$Q^4$ group is in the meta or para position;

$R^1$ and $R^2$ are independently selected from H and $C_1$-$C_4$ alkyl;

$Q^1$ is —$(CH_2)_n$—;

n is 0 or 1;

$Q^2$ is selected from —NH—, —C(=O)NH—, —NHC(=O)—, —NH—C(=O)—NH—, and —$SO_2$NH—;

$Q^3$ is a single bond or a $C_1$-$C_4$ alkylene optionally substituted with OH;

$Q^4$ is selected from

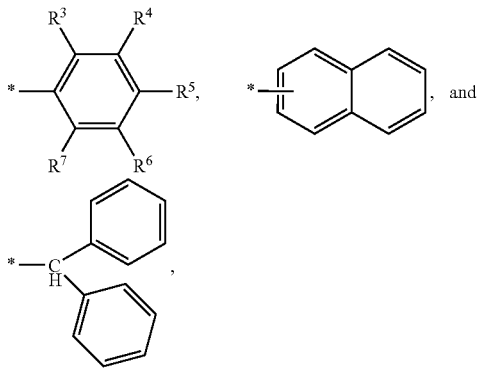

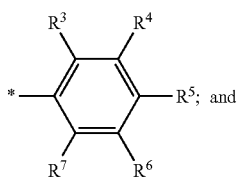

wherein * represents the attachment point to $Q^3$;

$R^3$, $R^4$, $R^5$, $R^6$ and $R^7$ are independently selected from H, $C_1$-$C_4$ alkyl, phenyl, phenoxy, $OR^8$, $SR^8$, halo, CN, $CF_3$, $OCF_3$, $COOR^9$, $SO_2NR^8R^9$, $CONR^8R^9$, $NR^8R^9$, $NHCOR^9$ and $CH_2$—$NHC(=O)NH$—$R^9$; and $R^8$ and $R^9$ are independently selected from H and $C_1$-$C_4$ alkyl; or a pharmaceutically acceptable salt, isomer, tautomer, solvate or isotopic variation thereof.

2. A compound according to claim 1, or a pharmaceutically acceptable salt thereof, wherein $Q^1$ is $(CH_2)_n$, n is 0 and $Q^2$ is —$SO_2NH$— or —$C(=O)NH$—.

3. A compound according to claim 1, or a pharmaceutically acceptable salt thereof, wherein $Q^1$ is $(CH_2)_n$, n is 1 and $Q^2$ is —NH—C(=O)— or —NH—C(=O)—NH—.

4. A compound according to claim 1, or a pharmaceutically acceptable salt thereof, wherein $Q^3$ is a bond, —$CH_2$—, —$(CH_2)_2$—, —$(CH_3)_2$—$CH_2$—, —$CH(CH_3)$—$CH(OH)$— or —$CH_2$—$CH(CH_3)$—.

5. A compound according to claim 1, or a pharmaceutically acceptable salt thereof, wherein $Q^4$ is

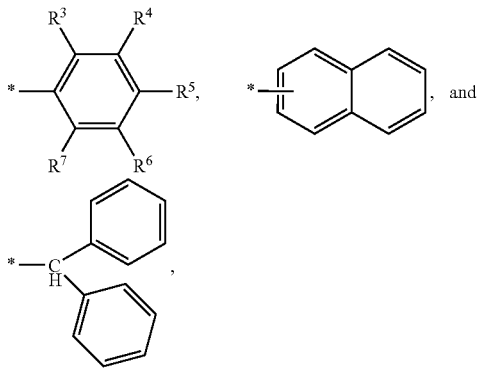 ; and $R^3$, $R^4$, $R^5$, $R^6$ and $R^7$ are selected from H, $C_1$-$C_4$ alkyl, phenyl, phenoxy, $OR^8$, $SR^8$, halo, $CF_3$, $OCF_3$, $COOR^9$, $SO_2NR^8R^9$, $CONR^8R^9$, $NHR^8R^9$, $NHCOR^9$ and $CH_2$—NHC(=O)NH—$R^9$; provided that at least two of $R^3$ to $R^7$ are H.

6. A compound according to claim 1, or a pharmaceutically acceptable salt thereof, wherein $R^1$ and $R^2$ are independently selected from H and $CH_3$.

7. The (R,R)-stereoisomer of a compound according to claim 1 or a pharmaceutically acceptable salt thereof.

8. A compound according to claim 1, or a pharmaceutically acceptable salt thereof, wherein the $CH_2$—C(=O)NH—benzyl-$Q^1$-$Q^2$-$Q^3Q^4$ group is in the meta position.

9. A compound according to claim 1, or a pharmaceutically acceptable salt thereof, selected from the group consisting of:

N-(4-tert-butylbenzyl)-4-{[({3-[(2R)-2-(2R)-2-hydroxy-2-[4-hydroxy-3-(hydroxymethyl) phenyl]ethyl}amino) propyl]phenyl}acetyl)amino]methy} benzamide;

N-(2-ethoxybenzyl)-4-{[({3-[(2R)-2-({(2R)-2-hydroxy-2-[4-hydroxy-3-(hydroxymethyl)phenyl]ethyl}amino)

propyl]phenyl}acetyl)amino]methyl} benzamide; 4-{[({3-[(2R)-2-({(2R)-2-hydroxy-2-[4-hydroxy-3-(hydroxymethyl)phenyl]ethyl} amino)propyl]phenyl}acetyl)amino]methyl-N-[4-(trifluoromethoxy)benzyl] benzamide;

N-(3,4-dichlorobenzyl)-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

N-[2-fluoro-5-(trifluoromethyl)benzyl]-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

N-[3,5-bis(trifluoromethyl)benzyl]-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

4-{]({3-[(2R)-2-({(2R)-2-hydroxy-2-[4-hydroxy-3-(hydroxymethyl)phenyl]ethyl}amino)propyl]phenyl}acetyl)amino]methyl}-N-(4-phenoxybenzyl)benzamide;

N-(1,1—dimethyl-2-phenylethyl)-4{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

N-[2-(4-ethylphenyl)ethyl]-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide N-[2-(4-chloronhenyl)ethyl]-4-{[({3-[(2R)-2-({(2R)-2-hydroxy-2-[4-hydroxy-3-(hydroxymethyl)phenyl]ethyl}amino)propyl]phenyl}acetyl)amino]methyl} benzamide;

N-[2-(4-ethoxyphenyl)ethyl]-4-{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

N-[2-(1,1'-biphenyl-4-yl)ethyl]-4{[({3-[(2R)-2-({(2R)-2-hydroxy-2-[4-hydroxy-3-(hydroxymethyl)phenyl]ethyl}amino)propyl]phenyl}acetyl)amino]methyl}benzamide;

4-{[({3-[(2R)-2-({(2R)-2-hydroxy-2-[4-hydroxy-3-(hydroxymethyl)phenyl]ethyl}amino)propyl]phenyl}acetyl)amino] methyl}-N-(4-hydroxy-3-methoxybenzyl) benzimide;

N-(1,1'-biphenyl-3-ylmethyl)-4-{[({3-[(2R)-2-({(2R)-2-hydroxy-2-[4-hydroxy-3-(hydroxymethyl)phenyl]ethyl}amino)propyl]phenyl}acetyl)amino]methyl{ benzimide;

4-{]({3-[(2R)-2-({(2R)-2-hydroxy-2-[4-hydroxy-3-(hydroxymethyl)phenyl]ethyl}amino)propyl]phenyl}acetyl)amino]methyl]-N-[2-(3-methoxyphenyl)ethyl] benzimide;

N-[2-(3,4-dichlprophenyl)ethyl]-4-{[({3-[(2R)-2-({(2R)-2-hydroxy-2-[4-hydroxy-3-(hydroxymethyl)phenyl]ethyl}amino)propyl]phenyl}acetyl)amino]methyl} benzimide;

4-{[({3-[(2R)-2-({(2R)-2-hydroxy-2-[4-hydroxy-3-(hydroxymethyl)phenyl]ethyl}amino)propyl]phenyl}acetyl)amino]methyl}-N-[(2S)-2-phenylpropyl}benzamide;

4-{]({3-[(2R)-2-[2R)-2-hydroxy-2-[4-hydroxy-3-(hydroxymethyl)phenyl]ethyl}amino)propyl]phenyl}acetyl)amino] methyl]-N-[(1R, 2S)-2-hydroxy-1-methyl-2-phenylethyl]benzimide;

4-ethoxy-N-(4{[({3-[(2R)-2-({(2R)-2-hydroxy-2-[4-hydroxy-3-(hydroxymethyl) phenyl]ethyl}amino)propyl]phenyl}acetyl)amino]methyl}benzyl)benzimide;

N-(4-{[({3-[(2R)-2-({(2R)-2-hydroxy-2-[4-hydroxy-3-(hydroxymethyl)phenyl]ethyl}amino)propyl]phenyl}acetyl)amino]methyl}benzyl)-1-naphthamide;

N-(4-{[({3-[(2R)-2-({(2R)-2-hydroxy-2-[4-hydroxy-3-(hydroxymethyl)phenyl]ethyl}amino)propyl]phenyl}acetyl)amino]methyl}benzyl)-2,2-diphenylacetamide;

N-(4-{[({3-[(2R)-2-({(2R)-2-hydroxy-2-[4-hydroxy-3-(hydroxymethyl)phenyl]ethyl}amino)propyl]phenyl}acetyl)amino]methyl}benzyl)-4-phenoxybenzimide;

N-{4-[(benzhydrylamino)methyl]benzyl]-2-{3-[(2R)-2-({(2R)-2-hydroxy-2-[4hydroxy-3 -(hydroxymethyl)phenyl]ethyl}amino)propyl]phenyl)acetamide;

N-{3-[(benzylamino)sulfonyl]benzyl]-2-{3-[(2R)-2-({(2R)-2-hydroxy-2-[4-hydroxy-3-(hydroxymethyl)phenyl]ethyl}amino)propyl]phenyl}acetamide;

2-{3-[(2R)-2-({(2R)-2-hydroxy-2-[4-hydroxy-3-(hydroxymethyl)phenyl]ethyl}amino)propyl]phenyl]-N-{4-[({[(3-phenoxybenzyl)amino]carbonyl}amino)methyl]benzyl}acetamide; and N-(3,4-dimethoxybenzyl)-4-{[({3-[(2R)-2-({(2R)-2-hydroxy-2-[4-hydroxy-3-(hydroxymethyl)phenyl]ethyl}amino)propyl]phenyl}acetyl)amino]methyl{ benzamide.

10. A method of treating a disease, disorder or condition in a mammal, which method comprises administering to said mammal an effective amount of a compound of claim 1 or a pharmaceutically acceptable salt thereof, said disease, disorder or condition being selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome, bronchiolytis, chronic or acute bronchoconstriction, chronic bronchitis, small airways obstruction, emphysema, chronic eosinophilic pneumonia, chronic obstructive pulmonary disease (COPD), COPD that includes chronic bronchitis, pulmonary emphysema not associated with COPD, pulmonary emphysema associated with COPD, dyspnea not associated with COPD, dyspnea associated with COPD, COPD that is characterized by irreversible, progressive airways obstruction, adult respiratory distress syndrome (ARDS), exacerbation of airways hyperreactivity consequent to other drug therapy, airways disease that is associated with pulmonary hypertension, chronic bronchitis, acute bronchitis, acute laryngotracheal bronchitis, arachidic bronchitis, catarrhal bronchitis, croupus bronchitis, dry bronchitis, infectious asthmatic bronchitis, productive bronchitis, staphylococcus bronchitis, streptococcal bronchitis, vesicular bronchitis, cylindric bronchiectasis, sacculated bronchiectasis, fusiform bronchiectasis, capillary bronchiectasis, cystic bronchiectasis, dry bronchiectasis, and follicular bronchiectasis.

11. A pharmaceutical composition comprising a combination of a compound according to claim 1 with a therapeutic agent selected from:

(a) 5-Lipoxygenase (5-LO) inhibitors or 5-lipoxygenase activating protein (FLAP) antagonists,
(b) Leukotriene antagonists (LTRAs) including antagonists of $LTB_4$, $LTC_4$, $LTC_4$, and $LTE_4$,
(c) Histamine receptor antagonists including H1 and H3 antagonists,
(d) $\alpha_1$- AND $\alpha_2$-adrenoceptor agonist vasoconstrictor sympathomimetic agents for decongestant use,
(e) muscarinic M3 receptor antagonists or anticholinergic agents,
(f) PDE inhibitors, e.g. PDE3, PDE4 and PDE5 inhibitors,
(g) Theophylline,
(h) Sodium cromoglycate,
(i) COX inhibitors both non-selective and selective COX-1 or COX-2 inhibitors (NSAIDs),
(j) Oral and inhaled glucocorticosteroids,
(k) Monoclonal antibodies active against endogenous inflammatory entities,
(l) Anti-tumor necrosis factor (anti-TNF-$\alpha$) agents,
(m) Adhesion molecule inhibitors including VLA-4 antagonists,
(n) Kinin-$B_1$- and $B_2$-receptor antagonists,
(o) immunosuppressive agents,
(p) Inhibitors of matrix metalloproteases (MMPs),
(q) Tachykinin $NK_1$, $NK_2$ and $NK_3$ receptor antagonists,
(r) Elastase inhibitors,
(s) Adenosine A2a receptor agonists,
(t) Inhibitors of urokinase,
(u) Compounds that act on dopamine receptors, e.g. D2 agonists,
(v) Modulators of the $NF_k\beta$ pathway, e.g. IKK inhibitors,
(w) modulators of cytokine signalling pathways such as p38 MAP kinase or syk kinase,
(x) Agents that can be classed as mucolytics or anti-tussive, and antibiotics.

12. A method according to claim 10 wherein said disease, condition or disorder is selected from asthma and chronic obstructive pulmonary disease (COPD).

* * * * *